United States Patent
Fan et al.

(10) Patent No.: US 6,689,609 B1
(45) Date of Patent: *Feb. 10, 2004

(54) ENHANCING GERMINATION OF PLANT SOMATIC EMBRYOS BY PRIMING

(75) Inventors: Shihe Fan, Vancouver (CA); Vesna Janic, Vancouver (CA)

(73) Assignee: Cellfor Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/550,110

(22) Filed: Apr. 14, 2000

Related U.S. Application Data

(60) Provisional application No. 60/129,492, filed on Apr. 15, 1999.

(51) Int. Cl.⁷ ............................................. C12N 5/00
(52) U.S. Cl. ..................... 435/422; 47/57.6; 504/116.1
(58) Field of Search ............... 435/422; 504/116.1; 47/57.6

(56) References Cited

U.S. PATENT DOCUMENTS

| | | |
|---|---|---|
| 4,583,320 A | 4/1986 | Redenbaugh |
| 4,777,762 A | 10/1988 | Redenbaugh |
| 4,780,987 A | 11/1988 | Nelson et al. |
| 4,957,866 A | 9/1990 | Gupta et al. |
| 5,010,685 A | 4/1991 | Sakamoto et al. |
| 5,119,588 A | 6/1992 | Timmis et al. |
| 5,183,757 A | 2/1993 | Roberts |
| 5,236,469 A | 8/1993 | Carlson et al. |
| 5,294,549 A | 3/1994 | Pullman et al. |
| 5,413,930 A | 5/1995 | Becwar et al. |
| 5,427,593 A | 6/1995 | Carlson et al. |
| 5,451,241 A | 9/1995 | Carlson et al. |
| 5,464,769 A | 11/1995 | Attree et al. |
| 5,482,857 A * | 1/1996 | Gupta et al. ............. 435/240 |
| 5,486,218 A | 1/1996 | Carlson et al. |
| 5,491,090 A | 2/1996 | Handley, III et al. |
| 5,506,136 A | 4/1996 | Becwar et al. |
| 5,563,061 A | 10/1996 | Gupta |
| 5,677,185 A | 10/1997 | Handley, III |

FOREIGN PATENT DOCUMENTS

| | | |
|---|---|---|
| WO | WO 93/11660 | 6/1993 |
| WO | WO 94/24847 | 11/1994 |
| WO | WO 96/37095 | 11/1996 |
| WO | WO 98/57536 | 12/1998 |

OTHER PUBLICATIONS

Germination of Alfafa (Medicago sativa L.) Seeds and dessicated Somatic Embryos I. Mobilization of storage Reserves. Lai F.M. et al. J. Plant Physiol. vol. 145 pp 507–513 1995.*

Germination of Alfafa (Medicago sativa L.) Seeds and dessicated Somatic Embryos II. Effect of Nutrient Supplements Lai F.M. et al. J. Plant Physiol. vol. 146 pp 731–735 1995.*

Hormonal control of somatic embryo Philip Ammirato Plant physiology (1977) 59 579–586.*

Artificial seeds for plant propagation Jo Ann A. Fujiiet al. Tib Tech Dec. 1987 vol 5 335–339.*

McDonald, M.B. *2000 Seed Priming IN; Seed Technology and Its Biological Basis*. M.B.ack & J.D. Bewley (Eds.) Sheffield Academic Press (in press).

* cited by examiner

*Primary Examiner*—Bruce R. Campell
*Assistant Examiner*—Annette Para

(57) ABSTRACT

A process of nutripriming plant somatic embryos prior to sowing, comprising contacting an imbibed plant somatic embryo with a solution containing one or more dissolved nutrients, preferably including sucrose as one of the nutrients. The invention includes germinated embryos produced by the process, and a method of producing seedlings or full-grown plants incorporating the nutripriming step. The method preferably makes use of a growth medium containing the nutrient or nutrients used in the nutripriming step.

86 Claims, No Drawings

ENHANCING GERMINATION OF PLANT SOMATIC EMBRYOS BY PRIMING

CROSS-REFERENCE TO RELATED APPLICATION

This application claims the priority right of U.S. Provisional application Serial No. 60/129,492 filed Apr. 15, 1999 by applicants named herein.

TECHNICAL FIELD

This invention relates to the germination of plant somatic embryos. More particularly, the invention relates to a process of treating plant somatic embryos with a nutripriming step to enhance subsequent germination of such embryos.

BACKGROUND OF THE INVENTION

A plant seed is a complete self-contained reproductive unit generally consisting of a zygotic embryo, storage reserves of nutrients in structures referred to as cotyledons, endosperm or megagametophytes, and a protective seed coat encompassing the storage reserves and embryo. In nature, maturation of plant seeds is usually accompanied by gradual loss of water over a period of time to levels between 10–35% moisture content. Once these low moisture levels are achieved, plant seeds can be stored for extended periods.

Germination of zygotic plant seeds is generally triggered by one or more environmental cues such as the presence of water, oxygen, optimal temperature, and light. Seeds germinate by means of a series of events which commence with the uptake of water by a quiescent dry seed and then subsequently proceed through various biophysical, biochemical and physiological events which ultimately result in the elongation of the embryo along its axis.

For the purpose of simplifying discussion of the present invention, the continuous process of seed germination is divided into three phases. Phase one is referred to as imbibition and is characterized by a rapid initial influx of water into the seed. Other significant events occurring in Phase one are the initiation of repair to damage to DNA and mitochondria which may have occurred during seed desiccation and/or the maturation process, and subsequent commencement of protein synthesis facilitated by existing mRNA.

Phase two is characterized by a significant reduction in the rate of water uptake (i.e., imbibition has been completed). This is accompanied by activation or de novo synthesis of enzymes that specialize in hydrolyzing the complex storage reserves of carbohydrates, proteins, and lipids in the embryo and the cotyledons or megagametophytes. The hydrolysis of these complex storage reserves provides the substrates required for the respiration and growth of the zygotic embryos.

Phase three is characterized by a second rapid increase in the rate of water uptake. Water absorbed during Phase three is used primarily for the initiation of meristomatic cell division at the root and shoot apices of the embryo, and for uptake into the cells along the embryonal axis. Water taken up by the axial cells of the embryo applies turgor pressure which results in axial cell elongation. The net effect is that the embryo elongates to the point of protrusion through the seed coat. Protusion of a shoot or root radicle through the seed coat signifies the completion of germination and the onset of seedling growth and development.

The speed and success for germination of zygotic seeds can fluctuate considerably depending on various factors such as the residual influence of environmental conditions in which the seed developed and maturated, the amount of storage reserve compounds synthesized during the seed maturation process, the duration of storage, and the quality of the storage environment (e.g., temperature and humidity). From a commercial perspective, it is desirable to reduce the risk of germination failure and to ensure that seeds germinate rapidly and uniformly.

The commercial need for optimum seed germination performance has led to the development of processes known in the art for zygotic seeds as "seed priming". This term may be defined as the "uptake of water to initiate the early events of germination, but not sufficient to permit radicle protrusion, preferably followed by drying" (McDonald, 2000). Four techniques are currently used commercially to accomplish seed priming. These are hydropriming, osmopriming, matripriming and pregermination. However, regardless of the method used, the fundamental principles of seed priming are that: (1) the preliminary stages of germination are activated specifically and exclusively through controlling the availability of water to the seeds, and (2) the germination processes initated through an external priming process are subsequently arrested by a desiccation step.

One of the problems with commercializing somatic embryo technologies has been a relatively low rate of conversion to seedlings and low seedling vigor when conversion takes place. It would clearly be advantageous to improve such rates of conversion and levels of seedling vigor.

However, a significant additional problem is the current inability to use conventional horticultural ex vitro techniques, practices and environments for the sowing and germinating of plant somatic embryos. The main reason for the difficulties in successfully germinating plant somatic embryos in non-sterile commercial growing environments using conventional propagation practices is that during the intitial stages of germination, matured plant somatic embryos cannot produce their own carbon compounds or derive energy from photosynthesis. Furthermore, they lack the presence of their own energy and nutrient sources that are equivalent to storage reserves contained within cotyledons or endosperm or megagametophyte tissues in zygotic seeds. Consequently, an exogenous source of energy in the form of a selected sugar within a culture medium and other nutrients, must be supplied to the plant somatic embryos for successful germination to occur. Such culture media are highly susceptible to invasion by microorganisms which inevitably result in death or interfere with embryo survival and germination. Consequently, sowing and successful germination of plant somatic embryos on culture media must be conducted under strict aseptic conditions.

Although numerous protocols are known for the sowing and germination of somatic embryos and growing them into intact functional seedlings, all of these protocols are dependent on the use of aseptic techniques combined with in vitro systems that must be kept in biological isolation from contaminating microorgansisms and fungi until the plant somatic embryos have successfully completed germination and have achieved autotrophy. Consequently, none of these protocols has demonstrated compatibility with conventional horticultural equipment and practices.

Generally, the known protocols for germinating somatic embryos fall into two categories. The first is a category of protocols based on various in vitro methods which generally are comprised of sowing naked, i.e., uncoated, somatic embryos using aseptic techniques, onto sterilized semi-solid or liquid media contained within a solid-support such as a petri dish or a phytatray to facilitate germination under biologically isolated sterile conditions (e.g., U.S. Pat. Nos. 5,183,757; 5,294,549; 5,413,930; 5,464,769; 5,506,136 all of which are herein incorporated by reference) and subsequently, transplanting the germinants into conventional growing systems. The most significant disadvantages of such in vitro protocols for sowing naked somatic embryos are that (a) each embryo typically must be handled and manipulated by hand for the germination and transplanting steps, and (b) aseptic techniques and culture conditions must be rigorously maintained through to the step of transplanting of somatic germinants out of the in vitro germination media into horticultural growing media. Although various automation options, including robotics and machine vision, have been assessed for their usefulness in cost-effective reduction or elimination of the extensive hand-handling currently necessary to sow naked embryos (Roberts et al., 1995), no commercial equipment currently exists which can reliably, aseptically, and cost-effectively perform the in vitro protocols for germination of naked somatic embryos and subsequent transplanting into conventional propagation systems.

The second category of protocols teach encapsulation (generally gel-encapsulation) of somatic embryos (e.g., U.S. Pat. Nos. 4,777,762; 4,957,866; 5,183,757; 5,482,857 all of which are herein incorporated by reference) to provide a means by which the embryos can presumably be sown with mechanical devices such as seeders and fluidized drills, into conventional growing systems. However, there are a number of disadvantages with gel-encapsulated somatic embryos. For example, the hydrated semi-solid physical characteristics of encapsulated embryos make them incompatible for use with conventional seeding equipment currently available for commercial plant propagation, because the semi-solid gel-encapsulated somatic embryos tend to clump together during handling and consequently, are difficult to singulate and dispense. Furthermore, compositions of encapsulated embryos prepared as taught by the art, clog-up the conventional equipment, and for these reasons, it currently is not possible to sow encapsulated embryos with conventional seeding equipment. Consequently, novel equipment has been developed specifically for delivery of encapsulated somatic embryos into conventional growing systems. Such sowing devices have been reviewed by Sakamoto et al. (1995), but these devices have only been developed and tested as prototypes. Because of mechanical limitations and the high costs associated with the prototype mechanical seeders developed for sowing encapsulated embryos, none are currently available for commercial acquisition and use.

Another disadvantage with encapsulated somatic embryos is the lack of nutrient availability that is characteristically supplied to zygotic embryos by their attendant endosperm or megagametophyte tissues. Consequently, the encapsulation technology for somatic embryos has been extended to include the incorporation of various nutrients such as sugars, fertilizers, oxygen, into the encapsulation medium (e.g., Carlson & Hartle, 1995; U.S. Pat. Nos. 4,583,320; 5,010,685; 5,236,469, all of which are herein incorporated by reference). However, a distinct disadvantage associated with nutrient-amended encapsulated embryos is their susceptibility to microbial invasion during manufacture, storage, and during germination if germinated on non-sterile media.

Furthermore, it must be pointed out that although considerable prior art (e.g., PCT Patent Application WO 94/24847, and U.S. Pat. Nos. 5,010,685; 5,236,469; 5,427,593; 5,451,241; 5,486,218 all of which are herein incorporated by reference) teaches methods to manufacture "artificial seeds" consisting of somatic embryos encapsulated in gels, which may or may not be optionally supplemented with nutrients, and which may or may not be encased within a rigid covering, and although the prior art makes references to sowing said artificial seeds ex vitro into germination media comprised of soil or soil-less mixes, the prior art only teaches methods for germinating said artificial seeds in vitro, i.e., on sterilized semi-solid laboratory media. No methods are taught or otherwise disclosed in the prior art for sowing said encapsulated somatic embryos and/or manufactured and/or artificial seed into conventional growing systems using conventional sowing equipment.

However, the most significant disadvantage with all prior art procedures for encapsulating or otherwise coating somatic embryos, is that somatic embryos processed following those protocols typically have, as a consequence, much lower germination vigor and success than corresponding zygotic seeds (Carlson & Hartle, 1995). Carlson and Hartle (1995) concluded that considerable research is still required before "manufactured" or "artificial" seeds based on encapsulation and/or coating of somatic embryos will have practical utility. However, it should be noted that the germination vigor of naked, i.e., un-coated or non-encapsulated somatic embryos produced with methods disclosed in the art and then sown using aseptic technique onto in vitro germination media and subsequently germinated in sterile conditions, can approximate those of the corresponding zygotic seeds (e.g., greater than 85%) (Gupta & Grob, 1995).

Timmis et. al. (U.S. Pat. No. 5,119,588 incorporated herein by reference) teach a method by which plant somatic embryos can be sown into horticultural containers filled with particulate soil-like substrates. Solutions containing carbon compounds serving as energy sources and other nutrients are added to the substrates before or after the embryos are sown. However, they teach that it is essential that the containers, substrate, nutrient solutions and other components of their system must be biologically sterile. Furthermore, once the somatic embryos are sown into their system using aseptic techniques, each individual container must be kept biologically separated from the others and from the external environment and must be kept in a sterile condition until the embryo has successfully germinated, formed functional roots and shoots and has accomplished autotrophy. Only after autotrophy has been reached can the somatic seedlings be removed from the sterile conditions within their system, and then transplanted into a conventional commercial propagation environment.

Even though it is possible to successfully germinate plant somatic embryos on culture media using aseptic techniques and subsequently transplant the germinants into nursery production environments, such methods are labor-intensive, slow and very costly. Furthermore, somatic embryos obtained in accordance with the prior art are not amenable to the systems and equipment commonly used for commercial production of plant material. Therefore, there is still a need for a practical method of supplying exogenous energy and nutrient sources to plant somatic embryos in a manner that will facilitate and maximize the ex vitro germination of somatic embryos and the subsequent plant development and growth under non-sterile conditions.

SUMMARY OF THE INVENTION

An object of the invention is to enhance germination of plant somatic embryos.

Another object of the invention is to improve the reliability and synchronization of plant somatic embryo germination.

Another object of the invention is to facilitate the growth of plants and seedlings from plant somatic embryos.

Another object of the invention is to enable the germination of plant somatic embryos to occur in non-sterile conditions in growing media commonly used in commercial nursery practice.

According to one aspect of the invention, there is provided a process of priming plant somatic embryos, which comprises contacting mature plant somatic embryos with an aqueous solution containing a dissolved nutrient.

The nutrient is preferably a carbohydrate, e.g. a sugar such as sucrose. When sucrose is employed as the priming nutrient, it is preferably used at a concentration in an aqueous medium of 6% w/v or less.

According to another aspect of the invention, there is provided a process of nutripriming plant somatic embryos prior to germination, comprising contacting imbibed plant somatic embryos with a solution comprising a mixture of two or more dissolved nutrients.

According to another aspect of the invention, there is provided a method of producing seedlings or full-grown plants from somatic embryos, which comprises nutripriming plant somatic embryos by contacting imbibed plant somatic embryos with a solution containing a dissolved nutrient, germinating the nutriprimed embryos in a growth medium to form germinants, and maintaining growing conditions to allow the germinants to grow into seedlings or full-grown plants.

According to another aspect of the invention, there is provided a method of producing seedlings or full-grown plants from somatic embryos, which comprises nutripriming plant somatic embryos by contacting imbibed plant somatic embryos with a solution containing a mixture of dissolved nutrients, germinating the nutriprimed embryos in a growth medium to form germinants, and maintaining growing conditions to allow the germinants to grow into seedlings or full-grown plants.

According to another aspect of the invention, there is provided a method of germinating mature plant somatic embryos, comprising priming imbibed embryos in the presence of a nutrient medium.

According to yet another aspect of the invention, there is provided a method of producing somatic seedlings, comprising (i) priming imbibed mature plant somatic embryos in a nutrient medium, and (ii) sowing the embryos in a growth medium.

The invention also relates to somatic embryos, seedlings or mature plants produced by the above methods.

The somatic embryo is preferably from a tree species, most preferably a gymnosperm, e.g. pine. The process is particularly effective with spruce and pine somatic embryos.

It is an advantage of the present invention, at least in preferred forms, that it can provide a process by which an imbibed somatic embryo can be nutriprimed in solutions containing one or more nutrients, then harvested from the nutripriming medium, and subsequently sown, germinated and grown ex vitro using conventional horticultural and agricultural equipment, containers, growing substrates, and growing environments. Furthermore, the sowing, germination and growing steps can be performed without the use of biologically isolating enclosures, or sterile media and growing environments. Alternatively, after the nutripriming step is completed, primed somatic embryos can be dried and stored for periods of time prior to ex vitro sowing and germination Another advantage of the invention, at least in preferred forms, is that it can provide a process by which the nutripriming of somatic embryos followed by harvesting and subsequent ex vitro sowing, germination and growing, can be practiced with a diverse variety of gymnosperm and angiosperm species. Alternatively, harvested nutriprimed somatic embryos of both gymnosperm and angiosperm species may be desiccated and stored for periods of time prior to ex vitro sowing and germination.

In preferred forms, the present invention relates to a multi-step process to produce seedlings from mature somatic embryos which begins by imbibing somatic embryos and then placing the imbibed somatic embryos into solutions containing nutrients for periods of time. This first component of the multi-step process is referred to as "nutripriming." It has surprisingly been found that nutriprimed somatic embryos can be sown ex vitro using various non-sterile methods into a wide variety of horticultural nursery containers filled with various types of non-sterile growing mixes commonly used in commercial horticultural and agricultural plant propagation. Once placed into conventional non-sterile nursery propagation systems and using conventional horticultural growing practices, the nutriprimed somatic embryos will germinate and grow into fully functional plants. Furthermore, we have surprisingly found that nutripriming solutions can be applied using conventional non-sterile horticultural equipment to facilitate and enhance the germination of nutriprimed somatic embryos.

We have also surprisingly discovered that nutriprimed somatic embryos can be desiccated to moisture contents in the range of 10–76%. Furthermore, we have discovered that desiccated nutriprimed somatic embryos can be stored for extended periods of time without significant declines in physiological integrity or germination potential. We have also discovered that desiccated nutriprimed somatic embryos are amenable for sowing with conventional seeding equipment into conventional plant propagation media for germination and further growth and development using conventional non-sterile plant propagation practices.

Consequently, the multi-step process of at least preferred forms of the present invention includes, but is not limited to, the steps of imbibing somatic embryos, nutripriming said imbibed somatic embryos, placing said nutriprimed somatic embryos into a state of physiological dormancy, sowing said nutriprimed physiologically dormant somatic embryos onto or into conventional horticultural germination substrates, propagating said sown nutriprimed somatic embryos in environmental conditions manipulated to facilitated imbibition, germination, and development into complete seedlings possessing shoots and roots.

There are several advantages inherent with the use of the process of the invention. For example, one advantage of nutripriming plant somatic embryos is that they show exceptional vigor during germination and subsequent development into complete seedlings possessing shoots and roots. Furthermore, desiccated nutriprimed somatic embryos are particularly useful for preserving the physiological viability of the embryos during extended storage prior to sowing and germination. Yet another advantage of nutripriming somatic embryos is that they can be sorted according to size, length and shape to facilitate production of more uniform crops after sowing, germination and growth.

A key advantage of the present process is that once the nutripriming step is completed, all subsequent components of the multi-step process can be practiced in conventional plant propagation environments without the need for aseptic handling processes or for sterile growing environments. More specifically, aseptic procedures, and sterile or sanitized equipment and germination/growing environments are not required for successful ex vitro sowing and. germination of nutriprimed somatic embryos and their subsequent development into complete functional seedlings, thus enabling the entire sowing, germination, and growing steps to be performed, if so desired, in commercial plant propagation or greenhouse or nursery growing facilities.

Another advantage is that the nutriprimed somatic embryos can be sown with conventional seeding equipment such as but not restricted to, vacuum-drum seeders, fluid-drill seeders or needle-jet seeders.

A further advantage is that commonly used horticultural and agricultural products such as, but not restricted to, soil-less seedling mixes or rock wool or foams, can be used as the supports onto which the nutriprimed somatic embryos are sown and subsequently germinate into and penetrate with their roots.

Most preferably, a nutrient (ideally the same nutrient as the one used in the nutripriming step) is also incorporated into said growth medium.

Yet a further advantage is that if necessitated by the conditions in the commercial growing environments, existing commercial pesticide products such as, but not restricted to fungicides, bactericides, antibiotics, nematicides, insecticides and the like, which are registered for use with the plant species from which the somatic embryos are produced, can be applied to the sown nutriprimed somatic embryos per label instructions for effective pest control, or alternatively, applied to the growing substrates prior to sowing the somatic embryos.

Another advantage is that exogenous nutrients necessary for successful somatic embryo germination and growth can be applied via the various numerous methods commonly used in commercial horticulture, said methods including but not restricted to misting, fogging, spraying, watering and drenching. Furthermore, said exogenous nutrients can be applied in conjunction with conventional horticultural fertigation practices.

This invention includes the above objects and features taken alone and in combination. These and other features, objects and advantages of the present invention will become more apparent with reference to the following description.

DEFINITIONS

A number of terms are known to have differing meanings when used in literature describing this art. The following definitions are believed to be ones most generally used in the fields of botany, plant somatic embryogenesis, and are consistent with the usage of the terms in the present specification.

These definitions will assist in the understanding of this detailed description.

"ABA" is absicic acid, a plant growth regulator.

"Autotrophic" refers to the stage of plant development when the photosynthetic organelles and related enzymes and biochemical pathways are fully functional and capable of converting light energy, atmospheric carbon dioxide and water into the pre-requisite carbohydrates (e.g., glucose) necessary to sustain further plant growth and development.

"BA" is benzyl adenine, a cytokinin-type of plant growth regulator. The main physiological effect of BA is to stimulate meristomatic cell division.

"Clone" when used in the context of plant propagation refers to a collection of individuals having the same genetic constitution, and are produced from a culture that arises from an individual explant.

"Embryogenic culture" is a plant cell or tissue culture capable of forming somatic embryos and regenerating plants via somatic embryogenesis.

"Endosperm" is haploid nutritive tissue of angiosperm seed, of maternal origin, within which the angiosperm zygotic embryos develop.

"Explant" is the organ, tissue or cells derived from a plant and cultured in vitro for the purposes of starting a plant cell or tissue culture.

"GA" is gibberellin, a group of related growth regulator isomers (e.g., $GA_3$, $GA_4$, $GA_7$) that is naturally synthesized as a normal part of plant metabolism. The main physiological effect of GA is to stimulate elongation of individual plant cells. Exogenous applications of GA can be used to stimulate, manipulate and accelerate the initiation and growth of shoots and roots.

"Germination" is the three-phase series of events which commences with the uptake of water by a quiescent dry seed and proceeds through various biophysical, biochemical and physiological events which result in the elongation of the embryo along its axis and ultimately concludes with the protuberance of a root or shoot radicle through the seed coat. Seed germination occurs in three phases. Phase one is characterized by a rapid initial influx of water into the seed accompanied by the initiation of repair to damaged DNA and mitochondria. Phase two is characterized by a significant reduction in the rate of water uptake accompanied by activation or de novo synthesis of enzymes that specialize in hydrolyzing the complex storage reserves of carbohydrates, proteins, and lipids in the embryo and the cotyledons or megagametophytes. The hydrolysis of these complex storage reserves during Phase two provides the substrates required for the respiration and growth of the zygotic embryos. Phase three is charactized by a second rapid increase in the rate of water uptake which is used primarily for the initiation of meristomatic cell division at the root and shoot apices of the embryo, and for uptake into the cells along the embryonal axis. The process of germination is complete when the embryo has elongated to the point of protrusion through the seed coat.

"Hydropriming" is a seed priming process by which seeds are misted or soaked in water and then dried back before they complete the germination process.

"IAA" is indole-acetic-acid, a auxin-type growth regulator naturally synthesized as normal part of plant metabolism. The main physiological effect of IAA is to stimulate meristomatic cell division. Exogenous applications of IAA can be used to stimulate, manipulate and accelerate the initiation and growth of shoots and roots.

"IBA" is indole-butyric-acid, a chemical analog of IAA. IBA can be used to affect the initiation of roots and shoots in the same manner as exogenous applications of IAA.

"Imbibition" is the absorption and/or adsorption of water by certain colloids present in seeds or embryos, which results in the swelling of the tissues and activation of enzymatic and physiological processes.

"Line" is another term for "clone".

"Matripriming" refers to the use of solid carriers with low matric water potentials to control the rate and/or the amount of water absorbed during a seed priming process.

"Megagametophyte" is haploid nutritive tissue of gymnosperm seed, of maternal origin, within which the gymnosperm zygotic embryos develop.

"Microdroplet" is small molecule of water or water-based solution contained within the fine spray produced by applying pressure to a drop of water or a water-based solution.

"Nutrients" are the inorganic micro- and macro-minerals, vitamins, hormones, organic supplements, and carbohydrates necessary for culture growth and somatic embryo germination.

"Nutrient solution" is water containing a dissolved nutrient or mixture of nutrients.

"Nutripriming" refers to a process of exposing a plant somatic embryo to a nutrient solution during the Phase two period of germination for a period of time sufficient to enable the embryo to absorb mineral and organic nutrients necessary to complete the Phase two and Phase three steps of germination.

"Osmopriming" refers to a method of soaking seeds in aerated osmotica of low water potential to control the rate and/or the amount of water absorbed during a seed priming process.

"Physiological dormancy" refers to the cessation of the normal metabolic processes, i.e., anabolism and catabolism, that are inherent in plant growth and development, in a manner that does not negatively affect viability.

"Pregermination" is a seed priming process which allows water availability to seeds to the point of shoot or root radicle protrusion from the seed coat, before the desiccation step is applied.

"Seed priming" refers to a process which controls and manipulates the water availability to seeds to initiate and affect the early events of germination, but not sufficient to permit radicle protrusion, which is subsequently followed by drying.

"Somatic embryogenesis" is the process of initiation and development of embryos in vitro from somatic cells and tissues.

"Somatic embryo" is an embryo formed in vitro from vegetative (somatic) cells by mitotic division of cells. Early stage somatic embryos are morphologically similar to immature zygotic embryos; a region of embryonal cells subtended by elongated suspensor cells. The embryonal cells develop into the mature somatic embryo.

"Zygotic embryo" is an embryo derived from the sexual fusion of gametic cells.

DETAILED DESCRIPTION OF THE PREFERRED EMBODIMENTS

In a preferred form, the present invention is generally a multi-step germination process for plant somatic embryos which enables the use of conventional horticultural practices, equipment and facilities, said process comprising but not restricted to, some or all of the following sequential steps:

1. Initiating Phase one of the germination process by imbibing desiccated mature plant somatic embryos. It is preferable that the rate of imbibition during Phase one is controlled through the use of a process such as matripriming. It is also preferable that this step is performed using aseptic techniques and sterile conditions.

2. Once the Phase one germination step, i.e., imbibition, has been completed, the imbibed plant somatic embryos are transferred to a vessel containing a liquid nutripriming solution. The nutripriming solution must contain at least one source of carbohydrate. Although the preferred carbohydrate is sucrose, preferably in the range of 3–6% (w/v), this invention can be practiced with sugars such as fructose, glucose, maltose, galactose, mannose, lactose and the like. Furthermore, the nutripriming solution may contain, if so desired, a mixture of two or more carbohydrates. If carbohydrates other than sucrose, or if mixtures of carbohydrates, are used in the nutripriming solution, then the appropriate concentrations of each carbohydrate should be determined in advance by the use of rate-selection studies. The design and performance of such rate-selection studies are known to those skilled in this art. Another key feature of the present invention is that in addition to carbohydrates, the nutripriming solutions may also contain, if so desired, other types of nutrients which may further facilitate the various biochemical and physiological processes occurring during germination Phases two and three. Such nutrients include but are not restricted to inorganic minerals, vitamins and hormones. A non-limiting example of how this can be practiced is by adding to a solution containing sucrose in the range of 3–6% (w/v), a mixture of mineral nutrients formulated to deliver but not restricted to 454 mg/l nitrogen, 81 mg/l phosphorus, 704 mg/l potassium, 50 mg/l calcium, 39 mg/l magnesium, 193 mg/l sulfur, 3 mg/l manganese, 0.5 mg/l zinc, 89 mg/l chlorine, 3 mg/l iron, 0.7 mg/l iodine, 0.6 mg/l boron, 0.01 mg/l molybdenum, 0.01 mg/l cobalt, and 0.01 mg/l copper. Furthermore if so desired, IBA a plant growth regulator, may be added alone at a concentration of 0.1 uM/l or in combination with one or both of GA and BA, each at a concentration of 0.1 uM/l. Also, Ascorbic acid (a.k.a. vitamin C) may be added if so desired, at a concentration in the range of 10–1000 uM/l. Furthermore, if so desired, pest control products such as antibiotics or fungicides may be added to the nutripriming solution. A non-limiting example is the addition of benlate (0.1 g/l) and/or ampinicillin (0.1 g/l). It is preferable during this step that the nutripriming solutions are sterilized prior to addition of the somatic embryos, and that aseptic technique is used when adding embryos to the nutripriming solution.

3. The imbibed embryos are nutriprimed in the nutripriming solution for a period of time preferably ranging from 6 hours to 168 hours, more preferably in the range of 48 to 96 hours and most preferably between 72 to 96 hours. It is also preferable throughout the nutripriming process, that the embryos are suspended within the nutripriming solutions and are kept in constant motion. A non-limiting example of how this might be accomplished is by securing the vessels containing the embryos and nutripriming solutions onto a shaker table which is revolving at a rate in the range of 10–120 rpm, preferably in the range of 30–60 rpm. It is possible to practice the nutripriming step in either the presence or absence of light. Since it is known in the art that zygotic seeds of certain plant species will germinate only in the dark while zygotic seeds of other plant species require light for successful germination, those skilled in the art will be able to determine if the nutripriming step should be illuminated for the plant somatic embryos with which they wish to practice this invention. It is preferable that the contents of the nutripriming vessels are maintained in a sterile condition during the nutripriming process.

4. Sowing the nutriprimed plant somatic embryos into nursery containers containing a three-phase conventional horticultural growing substrate, said three phases comprising solids, liquids and air. Commencing with this step, aseptic technique and sterile conditions are not required to successfully practice this invention.

5. Placing the nursery containers sown with nutriprimed plant somatic embryos, into a conventional plant propagation environment in which light, temperature, atmospheric humidity, and moisture content of the rooting substrate can be controlled and manipulated to enable and facilitate the re-germination of the somatic embryos and their further development into seedlings.

6. If so desired, supplying an aerosol in the form of a mist or spray, to the surface of the nursery containers sown with somatic embryos, said aerosol containing the necessary carbohydrate compounds required to sustain and facilitate completion of the Phase three germination processes of the somatic embryos.

7. Supplying in the forms of an aerosol and/or a liquid suspension and/or a liquid solution, the micro- and macro-mineral elements required to sustain and facilitate completion of the Phase three germination processes of the somatic embryos and their subsequent development into seedlings.

8. Adjusting as required during completion of the somatic embryo germination processes and subsequent development into seedlings, the ambient light intensity and diurnal photoperiod, temperature, atmospheric humidity and other such factors may be adjusted as required during somatic embryo germination and their conversion into fully functional seedlings.

Alternatively, at the completion of step 3, nutriprimed embryos may be removed from the nutripriming solutions and desiccated to a moisture content preferably in the range of 10% to 75%, more preferably in the range of 15% to 50% and most preferably in the range of 20% to 25%. For example, the embryos may be desiccated by pouring the nutripriming solutions with the nutriprimed embryos onto filter paper in a vacuum filter apparatus for the removal of the excess solution; other methods of desiccation are known to those skilled in the art. The filter paper with primed embryos on their surfaces can then be placed into "flow-through" desiccation chamber for a period of 3–96 hr, preferably 12–24 hr. After desiccation, the dried nutriprimed embryos can be stored in sealed, plastic-lined pouches. Although desiccated nutriprimed embryos can be stored at ambient temperatures, it is preferable that they are stored at refrigerated temperatures, e.g., 2 to 10° C., and most preferably, frozen e,g, −20 to −80° C. Although it is preferable to use aseptic technique during the desiccation and storage of nutriprimed embryos, it is not essential for the successful practice of this invention. Desiccated nutriprimed embryos can be removed from storage and sown ex vitro commencing with step 4 above.

A key feature of this novel process is that special hygienic and/or aseptic and/or sterile handling methods and/or equipment and/or facilities are not required to successfully handle, sow and germinate wet or desiccated nutriprimed plant somatic embryos. Accordingly, steps 4 through 8 may be carried out in non-sterile, unhygienic and/or septic conditions, i.e., those types of conditions typically encountered in conventional horticultural plant propagation environments.

Although the nutriprimed somatic embryos can be sown with all types of conventional seeding equipment used for sowing zygotic seeds, it is preferred to use equipment that dispenses singulated seed into multi-chambered nursery containers, commonly referred to as miniplug trays or cell-packs, said containers commonly used to produce plant plugs which can be mechanically transplanted into larger containers or into field-growing environments.

A key feature of the present invention, at least in its preferred forms, is that the sowing and propagation of nutriprimed somatic embryos can be practiced with a wide variety of non-sterilized growing substrates commonly used in conventional plant propagation. The preferred growing substrate is peat-based and has been formulated specifically for germination of zygotic seed and is exemplified by mixtures such as (a) 100% short-fiber peat product polymerized with a water-binding polymer, supplied by companies such as Grow Tech Inc. (San Juan Bautista, Calif. USA), Preforma Inc. (Oberlin, Ohio USA), (b) 15.2 cu.ft of peat, 8 cu.ft. of vermiculite, 680 grams of dolomite lime, and 300 grams of Micromax®, and (c) 16.2 cu.ft. of peat, 6.75 cu.ft. perlite, 4 cu.ft. vermiculite, 6 kilograms of dolomite lime, 1.5 kilograms of gypsum, 375 grams of potassium phosphate, 250 grams Micromax®, and 35 grams of wetting agent. Alternatively, commercially formulated mixes such as PRO-MIX-G® or PRO-MIX-PGX® (Premier Peat Moss Ltd. Montreal, PQ, Canada), Sunshine Mix #3 (Sun-Gro Horticulture Inc., Hubbard, Oreg., USA), and Redi-Earth® (The Scotts Co., Marysville, Ohio, USA) can also be used with the present invention. It is preferred that the peat-based growing substrate is moistened to a moisture content in the range of 59–75% and then dispensed into multi-chambered trays commonly used for production of plant plugs. Although examples of such trays include styrofoam #252 miniplug trays manufactured by Beaver Plastics Inc (Edmonton, AB, Canada) and hard plastic #288 or #512 miniplug trays manufactured by TLC Polyform Inc (Plymouth Minn., USA, 55441), the present invention can be practiced with other such multi-chambered trays, or alternatively, with individual pots. It should be noted that the practice of the present invention is not restricted to peat-based mixtures, but also includes other substrate such as Jiffy-7 peat plugs, composted or shredded coconut husk fibres commonly referred to as "cor" or "coir" (1993 Crystal Co., St. Louis, Mo., USA), extruded foams such as Oasis® (Smithers-Oasis Ltd., Kent, Ohio, USA), rock wool (Rockwool International A/S, Hovedgaden 584, DK-2640, Denmark) and the like. Regardless of the rooting substrate chosen, its physical characteristics should enable development and maintenance of a high relative humidity in the gaseous phase, i.e., in excess of 75% RH, within the substrate while minimizing saturation of the substrate with the liquid phase.

After the pre-germinated somatic embryos are sown onto the surfaces of the rooting substrates, if so desired, the embryos may be covered with a thin layer of additional rooting substrate that may be comprised of the same material underneath the embryos or alternatively, with a different type of material. One non-limiting example is sowing the pre-germinated embryos onto PRO-MIX-PGX® medium, then overlaying the embryos with a thin layer of coconut husk fibres.

Nursery containers sown with pre-germinated somatic embryos are preferentially placed into a conventional plant propagation environment wherein the conditions are within but not limited to the ranges of temperatures of 15–35° C., relative humidities of 75–100%, light intensities of 10–500 foot candles, and diurnal cycles of 6 h day/18 h night–22 h day/2 h night.

It is preferable to maintain a very high level of atmospheric humidity around the nursery containers sown with pre-germinated somatic embryos, i.e., greater than 90% RH, for the first 3–7 days after sowing to facilitate somatic embryo imbibition and germination. A number of methods can be used to maintain the atmospheric humidity at these levels including but not restricted to placing the containers in a greenhouse environment with misting or fogging equipment which is deployed at controlled intervals, placing the containers in a fogging or misting tent or chamber, placing clear plastic domes over the nursery containers and then removing domes periodically to mist or fog the sown embryos and replacing the domes immediately thereafter. Another non-limiting method is to provide a space ranging between 2 mm and 10 mm above the surface of the rooting substrate onto which the embryos are sown and the top of the container, and then covering the top of the nursery container with a plastic film which is removed to enable misting or fogging of the sown embryos and then immediately replaced. After somatic embryo germination is established as evidenced by development of epicotyl and root structures, the germinants can be weaned from the high relative humidity environments and integrated into conventional nursery cultural practices by gradually reducing the amount of misting/fogging applied and/or by extending the periods of time between the misting or fogging steps.

It is preferable to maintain the sown pre-germinated embryos in a high relative humidity environment, i.e., greater than 90% RH, for a period of, but not restricted to, 3–7 days after sowing to facilitate embryo imbibition, prior to supplying exogenous nutrients required for embryo germination.

Another key feature of the invention, at least in its preferred forms, is that the exogenous nutrients, including but not restricted to carbohydrates and minerals, required for successful somatic embryo re-germination and subsequent growth and development can be applied as aerosols. The nutrient solutions can be applied with, but not restricted to, conventional misting and/or fogging equipment. Although, the nutrients can be applied individually or combined into one solution, it is preferred to supply the carbohydrates as one solution and the remaining nutrients as a separate solution. A non-limiting example of how this can be practiced is by applying a 3% w/v sucrose solution as a mist to the surface of the growing substrate containing a sown pre-germinated embryo, and then applying at a later time, a solution containing a mixture of mineral nutrients formulated to deliver 454 mg/l nitrogen, 81 mg/l phosphorus, 704 mg/l potassium, 50 mg/l calcium, 39 mg/l magnesium, 193 mg/l sulfur, 3 mg/l manganese, 0.5 mg/l zinc, 89 mg/l chlorine, 3 mg/l iron, 0.7 mg/l iodine, 0.6 mg/l boron, 0.01 mg/l molybdenum, 0.01 mg/l cobalt, and 0.01 mg/l copper. Alternatively, the macronutrients can be supplied as a commercial formulation such as but not restricted to PlantProd® Plant Starter Fertilizer 10-52-10 (nitrogen-phosphate-potassium) or PlantProd® Forestry Seedling Starter 11-41-8 (nitrogen-phosphate-potassium) (Plant Products Ltd., Brampton, ON, Canada).

An alternative non-limited means of supplying exogenous nutrients to pre-germinated somatic embryos sown onto three-phase growing media within nursery containers is to irrigate or "drench" the media with nutrient solutions formulated as previously described.

Since microorganisms such as fungi, bacteria, yeast, and algae, are ubiquitous in conventional plant propagation substrates, equipment, containers and growing environments, a wide variety of chemical and biological pesticide products are available to control and irradicate plant pathogens. It has surprisingly been found that aseptic handling procedures and sterilized growing substrates, nursery containers and environments are not required to successfully germinate and grow plant somatic embryos. Indeed, the invention can be practiced in conventional plant propagation environments using only the standard commercial methods of hygiene. Furthermore, we have surprisingly found that pesticides such as Benlate®, Rovril®, Trumpet® and the like, which registered for pest control in plant crops, can be used in conjunction with somatic embryos pregerminated and subsequently sown with the present novel multi-step procedure.

The following Examples are provided to further illustrate the present invention and are not to be construed as limiting the invention in any manner.

EXAMPLE 1
Germination of Nutriprimed Interior Spruce Somatic Embryos on a Support With and Without Sucrose Supplements The objective of this study was to determine the effects of nutripriming treatments on the subsequent germination of interior spruce somatic embryos.

Post-HRHT (HRHT is a high-relative humidity treatment described by Roberts et al., 1993) somatic embryos of interior spruce genotype 1-1278 and 107-1917 were divided into groups of 80 embryos. Each group was separately placed into a 250-ml baffled flask containing 25 ml of m24GMD media (refer to Table 1.1 for the nutrient composition of m24GMD medium) with one of the following sucrose levels: 1, 2, 3, 4% (w/v). The flasks, after being stoppered with a stopper made from cotton and cheesecloth, were placed on a shaker and continuously shaken at 60 rpm and illuminated at 3040 mol $m^{-2}s^{-1}$ at the liquid surface height. The light was provided by two 25 W fluorescent bulbs. Ambient temperatures generally varied between 20–23° C. according to measurements. The embryos were nutriprimed for 3 days under these conditions.

After nutripriming was completed, the 80 embryos in each treatment were divided into 4 groups of 20 embryos. Each group was sown into a germination box as a replicate of respective treatments. The germination boxes were Sigma™ polycarbonate boxes. Each box contained 150 ml of horticulture coarse vermiculite and 120 ml m24GMD media without sucrose. Before use, the boxes were autoclaved for 20 minutes in a liquid cycle.

To prevent systematic errors that might have occurred had the experimental units not been randomized, each of the germination boxes housed a replicate from 4 different priming treatments. The assignment of the replicates into the germination boxes was facilitated using a random number table.

Nutriprimed embryos were hand-sown into the germination boxes. After sowing, the germination boxes were sealed twice with Parafilm™. Embryos were germinated and grown for one week under 50–70 $\mu$mol $m^{-2}s^{-1}$ photosynthetic photon flux of 16-hour photoperiod at an air temperature of 16° C. Then, the germinants were harvested and photocopies of the individual germinants were made. From these photocopies, germinant length was measured to the nearest 1 mm with a graph paper reproduced on a transparency.

The results are summarized in Table 1.2, from which the following observations were made:

1) After one week of germination on a vermiculite support without a sucrose supply, no visible changes were observed for the "control" embryos of interior spruce lines 1-1278 and 107-1917

2) All nutriprimed primed somatic embryos, regardless of nutripriming treatment, became green in colour with elongated epicotyls. Embryos nutriprimed in 3 and 4% w/v sucrose m24GMD elongated more than those primed in 1 and 2% w/v sucrose m24GMD with an exception in genotype 107-1917 whose germinants were the longest after priming in 2% w/v sucrose m24GMD.

3) None of the embryos sown in the germination boxes produced roots.

In summary, nutripriming priming treatment before germination is beneficial, but after sowing, root production requires an additional external sucrose supply.

TABLE 1.1

Nutrient composition of m24GMD medium. All weights are expressed in mg $l^{-1}$.

| Chemical | m.w. | wt. | N | P | K | Ca | Mg | S | Mn | Zn |
|---|---|---|---|---|---|---|---|---|---|---|
| $K_2SO_4$ | 174.2 | 275.0 | | | 123.4 | | | 50.5 | | |
| $CaCl_2.2H_2O$ | 147.0 | 183.77 | | | | 50.1 | | | | |
| $KNO_3$ | 101.1 | 2106.5 | 291.7 | | 814.6 | | | | | |
| $NH_4Cl$ | 53.49 | 382.1 | 100.0 | | | | | | | |
| $(NH_4)_2SO_4$ | 132.1 | 677.0 | 143.5 | | | | | 164.0 | | |
| $MgSO_4.7H_2O$ | 246.5 | 394.38 | | | | | 38.9 | 51.3 | | |
| $NH_4H_2PO_4$ | 115.0 | 1353.8 | 164.8 | 364.6 | | | | | | |
| $NaH_2PO_4.2H_2O$ | 156.0 | 35.5 | | 7.1 | | | | | | |
| $MnSO_4.4H_2O$ | 223.1 | 11.18 | | | | | | | 1.6 | 2.75 |
| $ZnSO_4.7H_2O$ | 287.6 | 2.04 | | | | | | | 0.3 | 0.46 |
| $CuSO_4.5H_2O$ | 249.7 | 0.025 | | | | | | | | |
| KI | 166.0 | 0.88 | | | | 0.2 | | | | |
| $CoCl.6H_2O$ | 202.5 | 0.024 | | | | | | | | |
| $H_3BO_3$ | 59.8 | 3.09 | | | | | | | | |
| $Na_2MoO_4.2H_2O$ | 241.9 | 0.024 | | | | | | | | |
| $FeSO_4.7H_2O$ | 278.0 | 13.90 | | | | | | | | |
| $Na_2EDTA$ | 372.2 | 18.61 | | | | | | | | |

TABLE 1.1-continued

Nutrient composition of m24GMD medium. All weights are expressed in mg $l^{-1}$.

| | | | | | | | | |
|---|---|---|---|---|---|---|---|---|
| Total amount | 700 | 371.6 | 938.2 | 50.1 | 38.9 | 267.6 | 2.75 | 0.46 |
| Rel. proportion | 100 | 53 | 134 | 7 | 6 | 38 | | |

| Chemical | Cl | Cu | Fe | B | Mo | Co | I | Na |
|---|---|---|---|---|---|---|---|---|
| $K_2SO_4$ | | | | | | | | |
| $CaCl_2.2H_2O$ | 88.6 | | | | | | | |
| $KNO_3$ | | | | | | | | |
| $NH_4Cl$ | 253.2 | | | | | | | |
| $(NH_4)_2SO_4$ | | | | | | | | |
| $MgSO_4.7H_2O$ | | | | | | | | |
| $NH_4H_2PO_4$ | | | | | | | | |
| $NaH_2PO_4.2H_2O$ | | | | | | | | 5.24 |
| $MnSO_4.4H_2O$ | | | | | | | | |
| $ZnSO_4.7H_2O$ | | | | | | | | |
| $CuSO_4.5H_2O$ | | 0.006 | | | | | | |
| KI | | | | | | | 0.67 | |
| $CoCl.6H_2O$ | 0.004 | | | | | 0.007 | | |
| $H_3BO_3$ | | | | 0.56 | | | | |
| $Na_2MoO_4.2H_2O$ | | | | | 0.01 | | | 0.002 |
| $FeSO_4.7H_2O$ | | | 2.79 | | | | | |
| $Na_2EDTA$ | | | | | | | | 1.15 |
| Total amount | 341.8 | 0.006 | 2.79 | 0.56 | 0.01 | 0.007 | 0.67 | 6.39 |

Notes:
1) $NO_3^-$—N: 291.7 mg $l^{-1}$.
2) $NH_4^+$—N: 408.3 mg $l^{-1}$.
3) The $NH_4^+$—N/$NO_3^-$—N ratio is 1.4
4) [N] = 50 mM; [P = 12 mM; [K] = 24 mM.

TABLE 1.2

Germinant length after one week growth on vermiculite support without sucrose supply

| Genotype | Nutripriming Treatment | Shoot Length (mm) |
|---|---|---|
| 1–1278 | HRHT | 3.2 ± 0.1 |
| | 1% w/v sucrose | 5.8 ± 0.3 |
| | 2% w/v sucrose | 5.8 ± 0.3 |
| | 3% w/v sucrose | 7.0 ± 0.3 |
| | 4% w/v sucrose | 7.3 ± 0.3 |
| 107–1917 | HRHT | 4.3 ± 0.2 |
| | 1% w/v sucrose | 7.8 ± 0.3 |
| | 2% w/v sucrose | 11.5 ± 1.7 |
| | 3% w/v sucrose | 8.4 ± 0.3 |
| | 4% w/v sucrose | 8.2 ± 0.5 |

EXAMPLE 2
Effects of Sucrose Levels in Nutripriming Solutions and Nutripriming Duration on the Germination and Growth of Interior Spruce Somatic Embryos The objective of this study was to determine the optimal sucrose level and nutripriming duration combination(s) that provide the best germination and growth of interior spruce somatic embryos.

Post-HRHT somatic embryos of interior spruce genotype 143-2695 were divided into groups of 60 embryos. Each group was separately placed in a 250-ml baffled flask containing 25 ml of m24GMD media with one of the following sucrose levels: 1, 2, 3, or 4% (w/v). Embryos were nutriprimed for 5 minutes (for the 2, 3, and 4% w/v sucrose levels only), 3 hours, 1, 2, 3, 4 or 5 days under conditions as specified in Example 1. This created various sucrose level x nutripriming duration combinations.

At the end of the nutripriming treatments, 10 embryos were randomly selected from each nutripriming treatment and measured for length. Then, the 60 embryos in each nutripriming treatment were divided into 4 groups of 15 embryos. Each group was sown into a germination box as a replicate of respective treatments. Each germination box contained 150 ml vermiculite and 120 ml 3% w/v sucrose m24GMD media and housed a randomly assigned replicate from 4 different nutripriming treatments. After sowing, embryos were germinated and grown for two weeks in a germination room under conditions as described in the previous example, after which, the germinants were harvested and measured.

The results are summarized in Tables 2.1–2.4, from which the following conclusions were made.

1) After two days in nutripriming treatment, somatic embryos started to elongate. The elongation was up to nearly 65% greater than the control treatments not receiving nutripriming. The elongation was similar in all four levels of sucrose nutripriming treatment (Table 2.1).
2) Hyperhydric rates increased with nutripriming duration and sucrose levels (Table 2.2).
3) Shoot growth of the germinants was stimulated by nutripriming treatments. The best growth occurred across all 4 sucrose levels when embryos were nutriprimed for 2 days (Table 2.3).
4) Although root growth of the germinants seemed to be optimal when embryos were nutriprimed for five days, the differences were small among all the nutripriming duration x sucrose levels (Table 2.4).
6) These results indicate significant interactions between nutripriming duration and sucrose levels in the nutripriming solution. Optimal germination and growth could be achieved by (a) combining lower sucrose levels in the nutripriming solutions with a longer period of nutripriming duration, or (b) higher sucrose levels in the nutripriming solutions would enable a shorter nutripriming duration.

TABLE 2.1

Effects of nutripriming treatments on germinant length (mm)

| Nutripriming period (days) | Control | 1% w/v sucrose | 2% w/v sucrose | 3% w/v sucrose | 4% w/v sucrose |
|---|---|---|---|---|---|
|   | 3.10 ± 0.09 |   |   |   |   |
| 1 |   | 3.23 ± 0.15 | 3.13 ± 0.16 | 3.06 ± 0.19 | 3.0 ± 0.15 |
| 2 |   | 3.44 ± 0.16 | 3.41 ± 0.12 | 3.47 ± 0.21 | 3.44 ± 0.15 |
| 3 |   | 3.99 ± 0.20 | 4.16 ± 0.21 | 3.9 ± 0.20 | 4.02 ± 0.10 |
| 4 |   | 5.21 ± 0.22 | 4.46 ± 0.20 | 4.18 ± 0.16 | 4.17 ± 0.19 |
| 5 |   | 4.8 ± 0.19 | 4.35 ± 0.30 | 4.39 ± 0.33 | 4.63 ± 0.19 |

TABLE 2.2

% hyperhydricity rates after a two-week germination period.

| Nutripriming Period | 1% w/v sucrose | 2% w/v sucrose | 3% w/v sucrose | 4% w/v sucrose |
|---|---|---|---|---|
| Control | 0.0 ± 0.0 | 0.0 ± 0.0 | 0.0 ± 0.0 | 0.0 ± 0.0 |
| 3 hr | 1.7 ± 1.7 | 5.0 ± 5.0 | 9.6 ± 3.2 | 0.0 ± 0.0 |
| 1 day | 8.3 ± 3.2 | 3.3 ± 3.3 | 6.3 ± 2.6 | 17.7 ± 6.4 |
| 2 day | 8.3 ± 8.3 | 4.6 ± 2.8 | 17.5 ± 8.5 | 8.3 ± 5.0 |
| 3 day | 11.7 ± 5.7 | 11.7 ± 3.7 | 16.0 ± 9.5 | 27.9 ± 6.7 |
| 4 day | 16.7 ± 7.9 | 56.7 ± 3.3 | 59.3 ± 6.6 | 69.1 ± 6.0 |
| 5 day | 29.2 ± 6.9 | 48.2 ± 7.4 | 71.7 ± 9.2 | 76.7 ± 6.4 |

TABLE 2.3

Shoot length after a two-week germination period (mm).

| Nutripriming duration | 1% w/v sucrose | 2% w/v sucrose | 3% w/v sucrose | 4% w/v sucrose |
|---|---|---|---|---|
| Control | 11.4 ± 0.4 | 14.5 ± 0.5 | 14.2 ± 0.4 | 16.0 ± 0.5 |
| 3 hr | 18.7 ± 0.5 | 16.8 ± 0.5 | 16.8 ± 0.6 | 16.7 ± 0.5 |
| 1 day | 17.2 ± 0.5 | 15.9 ± 0.3 | 17.3 ± 0.5 | 16.6 ± 0.5 |
| 2 day | 18.4 ± 0.6 | 17.5 ± 0.5 | 18.4 ± 0.6 | 18.0 ± 0.6 |
| 3 day | 16.5 ± 0.5 | 17.0 ± 0.4 | 16.6 ± 0.4 | 16.1 ± 0.5 |
| 4 day | 17.4 ± 0.6 | 16.2 ± 0.5 | 15.0 ± 0.3 | 16.0 ± 0.3 |
| 5 day | 20.9 ± 0.6 | 16.3 ± 0.5 | 14.4 ± 0.4 | 15.6 ± 0.4 |

TABLE 2.4

Root length measured at the end of two weeks of germination (mm)

| Nutripriming period | 1% w/v sucrose | 2% w/v sucrose | 3% w/v sucrose | 4% w/v sucrose |
|---|---|---|---|---|
| Control | 6.1 ± 0.4 | 6.9 ± 0.4 | 5.3 ± 0.5 | 6.7 ± 0.4 |
| 3 Hr | 8.0 ± 0.4 | 8.2 ± 0.5 | 5.8 ± 0.4 | 6.3 ± 0.4 |
| 1 day | 7.2 ± 0.4 | 6.0 ± 0.4 | 6.0 ± 0.5 | 7.2 ± 0.4 |
| 2 day | 6.5 ± 0.4 | 6.8 ± 0.3 | 7.7 ± 0.5 | 6.1 ± 0.4 |
| 3 day | 7.1 ± 0.4 | 6.8 ± 0.3 | 6.8 ± 0.4 | 5.4 ± 0.4 |
| 4 day | 7.4 ± 0.5 | 7.1 ± 0.5 | 5.7 ± 0.4 | 7.3 ± 0.4 |
| 5 day | 8.5 ± 0.3 | 8.9 ± 0.5 | 6.8 ± 0.5 | 8.0 ± 0.5 |

EXAMPLE 3

Effects of Nutripriming Solution pH on the Germination and Growth of Interior Spruce Embryos The objective of this study was to determine the optimal pH or pH range of the nutripriming solutions that does not negatively affect the germination of nutriprimed somatic embryos Post-HRHT somatic embryos of interior spruce genotype 4-2809 were divided into groups of 60 embryos and nutriprimed in 2% w/v sucrose m24GMD media for 3 days. The nutripriming solutions had pHs of 5.0, 5.5, 5.8, 6.0, 6.2, 6.5, 6.8, and 7.0 before autoclaving. The pH of each solution was re-measured 24 hours after autoclaving, just prior to and after the nutripriming treatments. After nutripriming, the embryos were sown into germination boxes and germinated in a germination room for two weeks as described in previous experiments. The germinants were then harvested and measured.

Autoclaving caused slight decreases in the pH of all nutripriming solutions (Table 3). After the 3-day nutripriming period, there were further declines in the pH of all nutripriming solutions. Germination of somatic embryos nutriprimed in nutripriming solutions with pHs in the range of 5.5–6.8 prior to autoclaving, was comparable or improved above the germination rates of the control un-nutriprimed embryos (Table 3). However, the germination percentage of embryos nutriprimed in solutions containing a starting pH 5 or less or 7 or greater was adversely affected. The rates of shoot and root development were not affected by the pH or changes in the pH of the various nutripriming solutions. Based on these results, it is evident that the pH of nutripriming solutions can be in the range of 5.5–6.8.

TABLE 3 pH changes before and after autoclaving, after nutripriming and the effects on the growth development of nutriprimed interior spruce somatic embryos.

| PH treatments | Before autoclaving | After autoclaving | After nutripriming | Germination % | Shoot length (cm) | Root length (cm) |
|---|---|---|---|---|---|---|
| HRHT | — | — | — | 89.0 ± 6.2 | 1.29 ± 0.03 | 0.86 ± 0.04 |
| 5.0 | 5.0 | 4.62 | 4.77 | 75.8 ± 9.6 | 1.05 ± 0.03 | 0.93 ± 0.03 |
| 5.5 | 5.5 | 5.17 | 4.78 | 95.0 ± 1.3 | 1.21 ± 0.03 | 0.87 ± 0.04 |
| 5.8 | 5.8 | 5.35 | 4.81 | 83.0 ± 7.1 | 1.08 ± 0.03 | 0.94 ± 0.04 |
| 6.0 | 6.0 | 5.61 | 4.89 | 97.5 ± 1.1 | 1.22 ± 0.03 | 0.95 ± 0.05 |
| 6.2 | 6.2 | 5.81 | 5.04 | 95.1 ± 2.2 | 1.08 ± 0.03 | 0.97 ± 0.03 |
| 6.5 | 6.5 | 6.13 | 5.63 | 93.3 ± 3.1 | 1.10 ± 0.03 | 1.00 ± 0.03 |
| 6.8 | 6.8 | 6.43 | 5.89 | 90.8 ± 3.7 | 1.10 ± 0.03 | 0.86 ± 0.03 |
| 7.0 | 7.0 | 6.57 | 6.14 | 73.3 ± 12.2 | 1.00 ± 0.07 | 0.91 ± 0.04 |

EXAMPLE 4

Effects of Nutripriming on Ex Vitro Germination and Rooting of Pine and Spruce Somatic Embryos Mature somatic embryos of interior spruce (*Picea glauca* (Moench) Voss x *P. engelmannii* Parry ex Engelm.), patula pine (*Pinus patula* Scheide et Deppe), radiata pine (*Pinus* radiata D. Don) and western white pine (*Pinus monticola* Dougl. ex D.Don) were desiccated with the HRHT treatment, and then nutriprimed in 3% w/v sucrose m24GMD solutions for 3 days under conditions as previously described. The nutriprimed somatic embryos, along with un-nutriprimed controls, were then sown ex vitro and grown for three weeks. In the first study, the embryos were sown into soil-less mixes consisting of 50% screened peat and 50% fine perlite in 288-cell miniplug trays (Blackmore Co.); each cell contained a volume of 10 ml. In the second study, the embryos were sown into 400-cavity styrofoam miniplug trays filled with peat bound by a polymer (Grow-Tech Inc., San Bautista, Calif.). After sowing, the horticultural containers were placed into a non-sterile high-humidity ($\geq$95% RH) germination chamber for one week with an 18-hour photoperiod of 30–40 mol $m^{-2}s^{-1}$ photosynthetic active radiation (PAR). In both studies, immediately after the trays containing ex vitro sown nutriprimed embryos were placed into the non-sterile high-humidity germination chamber, they were misted with m24GMD solution containing 3% w/v sucrose until the surfaces of the non-sterile growing substrates were well-wetted, and then at daily intervals for a period of 7 days. After the initial 7-day period in the non-sterile high-humidity germination environment, the trays were moved to a non-sterile misting chamber (RH ranged between 75–90%) for two more weeks of growth under an 18-hour photoperiod of 120–150 mol $m^{-2}s^{-1}$ PAR with day-night temperatures of 18–23° C. Daily applications of the m24GMD nutrient solution containing 3% w/v sucrose were misted onto the germinants through to the end of the two-week period in the misting chamber. Aseptic techniques or conditions were not used for application of the nutrient solutions, or for the germination and growing environments during the 3-week culture period.

At the end of the three-week germination period, all germinants were counted and examined for root initiation. Germination and rooting percentages were calculated based on the total number of embryos sown in each replicate. The rooting percentage measures the plant conversion rate since germinants can have perfectly elongated and formed shoot, but without root initiation. The variability in replication and number of embryos in each replicates among the experiments was caused by embryo or space availability at the time of the experimentation.

The results of these experiments are summarized in Table 4. It was clear that both post-HRHT and nutriprimed embryos can be directly sown ex vitro and grown in conventional non-sterile nursery environments. However, it was clearly evident that nutripriming treatments prior to ex vitro sowing could significantly increase the germination percentage and also increase the plant conversion rate when compared to the control post-HRHT treatments which were not nutriprimed.

TABLE 4

Effects of nutripriming on ex vitro germination and rooting of spruce and pine somatic embryos

| Species | Genotype | Cavities per plug tray | Embryo treatment | Germination % | % rooted |
|---|---|---|---|---|---|
| Interior spruce | 4–2809 | 288* | Control | 56.7 | 23.3 |
| | | | Nutriprimed | 75.6 | 62.4 |
| *Pinus patula* | 168–5074 | 288 | Control | 60.0 | 31.3 |
| | | | Nutriprimed | 88.1 | 54.2 |
| | 272–5071 | 288 | Control | 80.0 | 23.3 |
| | | | Nutriprimed | 100.0 | 45.6 |
| | 168–308 | 400** | Control | 52.3 | 6.9 |
| | | | Nutriprimed | 73.3 | 30.0 |
| *Pinus radiata* | B-7364 | 400 | Control | 51.4 | 5.6 |
| | | | Nutriprimed | 58.3 | 13.9 |

*Volume of each cavity in a #288 plug tray is 10 ml
**Volume of each cavity in a #400 plug tray is 3 ml

EXAMPLE 5

Ex Vitro Germination of Nutriprimed and Desiccated Somatic Embryos of Spruce and Pine.

Mature somatic embryos of interior spruce (*Picea glauca* (Moench) Voss x *P. engelmannii* Parry ex Engelm.), patula pine (*Pinus patula* Scheide et Deppe), and radiata pine (*Pinus radiata* D. Don) were desiccated with the HRHT treatment, and then nutriprimed for 3 days in 3% (interior spruce) or 4% w/v sucrose m24GMD (patula and radiata pines) solutions under conditions as previously described. After removal from the nutripriming solutions, the embryos were blotted dry on paper towels. The dried embryos were placed in Petri dishes. The dishes were then sealed in desiccation chambers containing unsaturated NaCl solutions, which provide varying relative humidity (RH) conditions as the molality of NaCl solutions changes. The embryos were desiccated in a 92.7% RH chamber at 23° C. in a Conviron chamber for 24 hours. Then, the embryos were transferred to a 88.5% RH chamber and desiccated for another 48 hours at 5° C. in a refrigerator. Before and after each desiccation treatment, 3 samples of 3 embryos were taken from each genotype and determined for water content (WC) and relative water content (RWC). After desiccation, the embryos were rehydrated first in a 100% RH chamber containing water and then on agar overnight. After rehydration, the desiccated nutriprimed embryos were sown into 400-cavity styrofoam miniplug trays filled with peat bound by a polymer (Grow-Tech Inc., San Bautista, Calif.). After sowing, the trays were placed into a non-sterile high-humidity ($\geq$95% RH) germination chamber for one week. In both studies, immediately after the trays containing ex vitro sown nutriprimed embryos were placed into the non-sterile high-humidity germination chamber, they were misted with m24GMD solution containing 3% w/v sucrose until the surfaces of the non-sterile growing substrates were well-wetted, and then at daily intervals for a period of 7 days. After the initial 7-day period in the non-sterile high-humidity germination environment, the trays were moved to a non-sterile misting chamber (RH ranged between 75–90%) for two more weeks of growth under an 1 8-hour photoperiod of 120–150 mol $m^{-2}s^{-1}$ PAR with day-night temperatures of 18–23° C. Daily applications of the m24GMD nutrient solution containing 3% w/v sucrose were misted onto the germinants through to the end of the two-week period in the misting chamber. Aseptic techniques or conditions were not used for application of the nutrient solutions, or for the germination and growing environments during the 3-week culture period.

At the end of the three-week germination period, all germinated embryos and seedlings were counted and examined for root initiation. Germination and rooting percentages were calculated based on total number of embryos sown in each replicate. The rooting percentage measures the plant conversion rate since the survived germinants can have perfectly elongated and formed shoot, but without root initiation.

The results of the experiment are summarized in Table 5. From these results, it is clear that nutriprimed somatic embryos can be desiccated, then sown ex vitro into non-sterile horticultural growing media and successfully germinated.

wetted, and then at daily intervals for a period of 7 days. After the initial 7-day period in the non-sterile high-humidity germination environment, the trays were moved to a non-sterile misting chamber (RH ranged between 75–90%) for two more weeks of growth under an 18-hour photoperiod of 120–150 mol $m^{-2}s^{-1}$ PAR with day-night temperatures of 18–23° C. Daily applications of the m24GMD nutrient solution containing 3% w/v sucrose were misted onto the germinants through to the end of the two-week period in the misting chamber. Aseptic techniques or conditions were not used for application of the nutrient solutions, nor for the germination and growing environments during the 3-week culture period.

At the end of the three-week germination period, all germinants were counted and examined for root initiation. Germination and rooting percentages were calculated based on the total number a of embryos sown in each replicate. The rooting percentage measures the plant conversion rate since

TABLE 5

Germination and rooting percentage of nutriprimed somatic embryos which were desiccated prior to ex vitro sowing and germination

| Species | Genotype | WC (%) Before desiccation | WC (%) After desiccation | RWC (%) Before desiccation | RWC (%) After desiccation | Germination (%) | Rooting percentage (%) |
|---|---|---|---|---|---|---|---|
| Interior spruce | 4-2809 | 230.5 ± 12.6 | 59.7 ± 4.9 | 61.6 ± 2.3 | 20.1 ± 1.5 | 52.6 ± 3.5 | 39.7 ± 6.9 |
| | 23-2672 | 235.7 ± 8.6 | 72.8 ± 3.9 | 75.9 ± 3.9 | 24.9 ± 2.4 | 68.3 ± 4.2 | 54.4 ± 4.8 |
| Patula pine | 168-308 | 266.9 ± 25.6 | 119.4 ± 18.2 | 84.8 ± 5.7 | 42.1 ± 3.6 | 74.4 ± 6.1 | 7.78 ± 6.2 |
| Radiata pine | 20-6609 | 270.9 ± 39.0 | 100.1 ± 12.8 | 75.1 ± 5.7 | 33.4 ± 3.6 | 88.8 ± 3.8 | 35.0 ± 5.0 |

EXAMPLE 6
Effects of Nutripriming on the Ex Vitro Germination of Spruce and Pine Somatic Embryos in Two Different Types of Non-sterile Horticultural Growing Substrates.

Mature somatic embryos of interior spruce (*Picea glauca* (Moench) Voss x *P. engelmannii* Parry ex Engelm.), patula pine (*Pinus patula* Scheide et Deppe), radiata pine (*Pinus radiata* D. Don), and, and western white pine (*Pinus monticola* Dougl. ex D.Don) were desiccated with the HRHT treatment, and then nutriprimed in 3% w/v sucrose m24GMD solutions for 3 days under conditions as previously described. Interior spruce line 4-2809 and *Pinus patula* lines 168-5074 and 2712-5071 nutriprimed somatic embryos, along with their un-nutriprimed HRHT controls, were then sown ex vitro into 288-cell miniplug trays (Blackmore Co.) containing a non-sterile horticultural growing mix comprised of 50% screened peat and 50% fine perlite. *Pinus patula* line 168-308, *Pinus radiata* line B-7364 and *Pinus monticola* line 212M-4572 were sown ex vitro into 400 cavity styrofoam miniplug trays filled with peat bound by a polymer (Grow-Tech Inc., San Bautista, Calif.). After sowing, the containers were placed into a non-sterile growth chamber for one week under 18 hour photoperiod of 30–40 mol $m^{-2}s^{-1}$ PAR. In both studies, immediately after the trays containing ex vitro sown nutriprimed embryos were placed into the non-sterile high-humidity germination chamber, they were misted with m24GMD solution containing 3% w/v sucrose until the surfaces of the non-sterile growing substrates were wellthe germinants can have perfectly elongated and formed shoot, but no root initiation The results for this study are summarized in Table 6. It was clearly evident that nutripriming somatic embryos prior to ex vitro sowing significantly improved germination percentage and increased the plant conversion rate when compared to the HRHT controls.

TABLE 6

Germination and rooting percentages of ex vitro sown HRHT control and nutriprimed somatic embryos of spruce and pine species.

| Species | Genotype | Embryo treatment | Miniplug tray type | Germination % | Rooting % |
|---|---|---|---|---|---|
| Interior spruce | 4-2809 | HRHT control | 288 cell | 56.7 | 23.3 |
| | | Nutriprimed | 288 cell | 75.6 | 62.4 |
| Pinus patula | 168–5074 | HRHT control | 288 cell | 60.0 | 31.3 |
| | | Nutriprimed | 288 cell | 88.1 | 54.2 |
| Pinus patula | 272–5071 | HRHT control | 288 cell | 80.0 | 23.3 |
| | | Nutriprimed | 288 cell | 100 | 45.6 |
| Pinus patula | 168–308 | HRHT control | 400 cell | 52.3 | 6.9 |
| | | Nutriprimed | 400 cell | 73.3 | 30.0 |
| Pinus radiata | B-7364 | HRHT control | 400 cell | 51.4 | 5.6 |
| | | Nutriprimed | 400 cell | 58.3 | 13.9 |
| Pinus | 22M-4572 | HRHT | 400 cell | 80.0 | 41.2 |

TABLE 6-continued

Germination and rooting percentages of ex vitro sown HRHT control and nutriprimed somatic embryos of spruce and pine species.

| Species | Genotype | Embryo treatment | Miniplug tray type | Germination % | Rooting % |
|---|---|---|---|---|---|
| monticola | | control | 400 cell | 56.7 | 50.0 |
| | | Nutriprimed | | | |

EXAMPLE 7
Effects of Ascorbic Acid on Germination and Development of Nutriprimed Interior Spruce Somatic Embryos Mature somatic embryos of interior spruce (*Picea glauca* (Moench) Voss x *P. engelmannii* Parry ex Engelm.) genotype 4-2809 were desiccated with the HRHT treatment, and then nutriprimed in 3% w/v sucrose m24GMD solutions for 3 days as previously described. The nutripriming solutions were formulated with one of the following three ascorbic acid treatments; 0, 10 uM, 100 uM.

The nutriprimed somatic embryos were then sown into germination boxes containing 150 ml vermiculite plus 120 ml of 3% w/v sucrose m24GMD liquid medium. The liquid medium added to the germination boxes contained one of four ascorbic acid leverls; 0, 10 uM, 100 uM or 1000 uM. Nutriprimed embryos from each ascorbic acid nutripriming treatment were then sown into triplicate boxes of each ascorbic acid-amended germination medium. After sowing, the germination boxes were sealed twice with Parafilm™. Embryos were germinated and grown for two weeks under 50–70 $\mu$mol m$^{-2}$s$^{-1}$ photosynthetic photon flux of 16-hour photoperiod at an air temperature of 22° C. Then, the germinants were harvested, and measured.

The effects of adding ascorbic acid on germination and rooting of nutriprimed interior spruce somatic embryo genotype 4-2809 are presented in Table 7. In this study the HRHT control somatic embryos germinated at very high percentages and consequently, improvements due to AA additions to the nutripriming and germination media were not significant. However, the rooting percentage was significantly increased in the somatic embryos which received nutripriming treatments containing ascorbic acid. Furthermore, it is evident that in this study, the largest rooting response was observed with embryos nutriprimed in solutions containing 10 uM ascorbic acid.

TABLE 7

Germination and growth of interior spruce genotype 4-2809 somatic embryos nutriprimed in solutions containing ascorbic acid (AA) and germinated on vermiculite media containing AA.

| AA level in germination media ($\mu$M) | AA level in priming solution ($\mu$M) | Germination % | Rooting % | Shoot length (cm) | Root length (cm) |
|---|---|---|---|---|---|
| 0 | HRHT | 100.0 ± 0.0 | 86.7 ± 8.8 | 2.17 ± 0.08 | 3.14 ± 0.38 |
| | 0 | 93.3 ± 3.3 | 86.7 ± 3.3 | 2.07 ± 0.11 | 2.60 ± 0.37 |
| | 10 | 100.0 ± 0.0 | 86.7 ± 3.3 | 1.86 ± 0.10 | 2.59 ± 0.26 |
| | 100 | 100.0 ± 0.0 | 96.7 ± 3.3 | 2.07 ± 0.11 | 3.56 ± 0.37 |

TABLE 7-continued

Germination and growth of interior spruce genotype 4-2809 somatic embryos nutriprimed in solutions containing ascorbic acid (AA) and germinated on vermiculite media containing AA.

| AA level in germination media ($\mu$M) | AA level in priming solution ($\mu$M) | Germination % | Rooting % | Shoot length (cm) | Root length (cm) |
|---|---|---|---|---|---|
| 1 | HRHT | 100.0 ± 0.0 | 75.6 ± 7.3 | 1.94 ± 0.09 | 2.44 ± 0.20 |
| | 0 | 96.7 ± 3.3 | 85.8 ± 3.0 | 1.68 ± 0.10 | 1.90 ± 0.23 |
| | 10 | 100.0 ± 0.0 | 86.7 ± 8.8 | 1.83 ± 0.11 | 2.07 ± 0.22 |
| | 100 | 100.0 ± 0.0 | 90.0 ± 0.0 | 1.79 ± 0.09 | 2.39 ± 0.28 |
| 10 | HRHT | 100.0 ± 0.0 | 75.0 ± 5.0 | 2.32 ± 0.15 | 3.70 ± 0.50 |
| | 0 | 97.5 ± 2.5 | 87.5 ± 6.3 | 1.84 ± 0.09 | 2.46 ± 0.30 |
| | 10 | 96.7 ± 3.3 | 86.7 ± 3.3 | 1.97 ± 0.19 | 2.82 ± 0.36 |
| | 100 | 100.0 ± 0.0 | 96.7 ± 3.3 | 2.33 ± 0.11 | 3.24 ± 0.32 |
| 100 | HRHT | 93.3 ± 6.7 | 68.5 ± 11.5 | 2.04 ± 0.12 | 3.51 ± 0.49 |
| | 0 | 93.3 ± 3.3 | 63.3 ± 8.8 | 1.81 ± 0.09 | 2.50 ± 0.33 |
| | 10 | 100.0 ± 0.0 | 78.2 ± 11.8 | 2.02 ± 0.11 | 3.18 ± 0.42 |
| | 100 | 100.0 ± 0.0 | 73.0 ± 11.8 | 2.12 ± 0.11 | 3.61 ± 0.39 |
| 1000 | HRHT | 100.0 ± 0.0 | 80.0 ± 5.8 | 2.05 ± 0.08 | 2.46 ± 0.30 |
| | 0 | 100.0 ± 0.0 | 90.0 ± 0.0 | 1.79 ± 0.14 | 2.11 ± 0.25 |
| | 10 | 100.0 ± 0.0 | 95.0 ± 5.0 | 2.00 ± 0.09 | 2.55 ± 0.20 |
| | 100 | 100.0 ± 0.0 | 90.0 ± 5.8 | 1.75 ± 0.15 | 2.19 ± 0.26 |

EXAMPLE 8
Effects of Growth Regulators on Germination and Development of Nutriprimed Somatic Embryos Mature somatic embryos of interior spruce (*Picea glauca* (Moench) Voss x *P. engelmannii* Parry ex Engelm.) genotypes 4-2809, 23-2672, and I-1026 were desiccated with the HRHT treatment. Genotype I-1026 was further desiccated at 85% RH for three days, then stored at -20C. Prior to nutripriming, genotype I-1026 was imbibed with a matripriming step which consisted of placing the desiccated embryos onto a screen, and then placing the screen on the surface of an agar substrate gelled with 3% phytogel for 18 hrs. After this imbibition step was completed for genotype I-1026, all three genotypes were nutriprimed for 84 hr in 3% w/v sucrose m24GMD nutripriming solutions amended with the plant growth regulators described in Table 8.1.

TABLE 8.1

Plant growth regulator amendments added to 3% w/v sucrose m24GMD nutripriming solutions

| | Growth regulators added to nutripriming solutions | | |
|---|---|---|---|
| Treatment # | IBA ($\mu$M) | BA ($\mu$M) | GA$_{4/7}$ ($\mu$M) |
| 1 | 0 | 0 | 0 |
| 2 | 0.1 | 0 | 0 |
| 3 | 0.05 | 0 | 0 |
| 4 | 0.05 | 0.01 | 0 |
| 5 | 0.05 | 0.01 | 0.01 |
| 6 | 0.05 | 0 | 0.05 |
| 7 | HRHT control | | |

After the nutripriming step was completed, the nutriprimed somatic embryos were sown ex vitro into 400-cavity styrofoam miniplug trays filled with peat bound by a polymer (Grow-Tech Inc., San Bautista, Calif.). After sowing, the trays were placed into a non-sterile high-humidity ($\geq 95\%$ RH) germination chamber for one week. In both studies, immediately after the trays containing ex vitro sown nutriprimed embryos were placed into the non-sterile high-humidity germination chamber, they were misted with m24GMD solution containing 3% w/v sucrose until the surfaces of the non-sterile growing substrates were well-wetted, and subsequently at daily intervals for a period of 7 days. After the initial 7-day period in the non-sterile high-humidity germination environment, the trays were moved to a non-sterile misting chamber (RH ranged between 75–90%) for two more weeks of growth under an 18-hour photoperiod of 120–150 mol m$^{-2}$s$^{-1}$ PAR with day-night temperatures of 18–23° C. Daily applications of the m24GMD nutrient solution containing 3% w/v sucrose were misted onto the germinants through to the end of the two-week period in the misting chamber. Aseptic techniques or conditions were not used for application of the nutrient solutions, or for the germination and growing environments during the 3-week culture period.

At the end of the three-week germination period, all germinated embryos and seedlings were counted and examined for root initiation. Germination and rooting percentages were calculated based on total number of embryos sown in each replicate. The rooting percentage measures the plant conversion rate since the survived germinants can have perfectly elongated and formed shoot, but without root initiation.

The results for this study are recorded in Table 8.2. The data indicate that for interior spruce genotype 4-2809, nutripriming significantly increased both germination and rooting percentages compared to the HRHT control treatment. Addition of supplemental growth regulators to the nutripriming solutions did not enhance germination and rooting performance of interior spruce genotype 4-2809 somatic embryos. However, a combination of 0.05 uM IBA plus 0.01 uM BA to solutions used to nutriprime genotype 23-2672 somatic embryos provided the highest germination response while the combinations of 0.05 uM IBA plus 0.01 uM BA, and combinations of 0.05 uM IBA plus 0.01 uM GA$_{4/7}$ provided the highest rooting percentage. Addition of 0.05 uM IBA to solutions used to nutriprime interior spruce genotype I-1026 provided the maximal germination and rooting response.

TABLE 8.2

Effects of plant growth regulators added to nutripriming solutions on ex vitro germination and development of nutriprimed interior spruce somatic embryos.

| Genotype | Dessication treatment | Nutririming treatment | IBA ($\mu$M) | BA ($\mu$M) | GA$_{4/7}$ ($\mu$M) | Germination % | Rooting % |
|---|---|---|---|---|---|---|---|
| 4-2809 | HRHT | Control | 0 | 0 | 0 | 32.5 ± 2.5 | 7.5 ± 2.5 |
| 4-2809 | HRHT | Primed | 0 | 0 | 0 | 96.3 ± 2.4 | 81.3 ± 3.1 |
| 4-2809 | HRHT | Primed | 0.1 | 0 | 0 | 68.8 ± 5.2 | 51.3 ± 4.3 |
| 4-2809 | HRHT | Primed | 0.05 | 0 | 0 | 92.5 ± 6.0 | 82.5 ± 6.0 |
| 4-2809 | HRHT | Primed | 0.05 | 0.01 | 0 | 80.0 ± 3.5 | 61.3 ± 4.7 |
| 4-2809 | HRHT | Primed | 0.05 | 0.01 | 0.01 | 85.0 ± 4.6 | 77.5 ± 3.2 |
| 4-2809 | HRHT | Primed | 0.05 | 0 | 0.05 | 75.0 ± 2.0 | 65.0 ± 7.4 |
| 23-2672 | HRHT | Control | 0 | 0 | 0 | 57.5 ± 7.5 | 40.0 ± 10.0 |
| 23-2672 | HRHT | Primed | 0 | 0 | 0 | 76.7 ± 2.4 | 64.8 ± 7.9 |
| 23-2672 | HRHT | Primed | 0.1 | 0 | 0 | 82.5 ± 9.7 | 72.5 ± 6.3 |
| 23-2672 | HRHT | Primed | 0.05 | 0 | 0 | 90.0 ± 3.5 | 71.3 ± 6.6 |
| 23-2672 | HRHT | Primed | 0.05 | 0.01 | 0 | 95.0 ± 2.9 | 75.0 ± 5.4 |
| 23-2672 | HRHT | Primed | 0.05 | 0.01 | 0.01 | 85.0 ± 3.5 | 72.5 ± 4.3 |
| 23-2672 | HRHT | Primed | 0.05 | 0 | 0.05 | 81.3 ± 7.5 | 75.0 ± 7.4 |
| I-1026 | 85% & frozen | Control | 0 | 0 | 0 | 87.5 ± 2.5 | 47.5 ± 7.5 |
| I-1026 | 85% & frozen | Primed | 0 | 0 | 0 | 78.8 ± 3.8 | 68.8 ± 5.2 |
| I-1026 | 85% & frozen | Primed | 0.1 | 0 | 0 | 88.8 ± 6.6 | 58.8 ± 5.9 |
| I-1026 | 85% & frozen | Primed | 0.05 | 0 | 0 | 93.8 ± 2.4 | 66.3 ± 4.7 |
| I-1026 | 85% & frozen | Primed | 0.05 | 0.01 | 0 | 77.5 ± 6.3 | 30.0 ± 7.4 |
| I-1026 | 85% & frozen | Primed | 0.05 | 0.01 | 0.01 | 73.8 ± 8.8 | 31.3 ± 2.4 |
| I-1026 | 85% & frozen | Primed | 0.05 | 0 | 0.05 | 63.8 ± 6.9 | 45.0 ± 5.8 |

The second study assessing the effects of plant growth regulators on germination performance of nutriprimed somatic embryos involved additions of plant growth regulators to the horticultural growing substrates after the nutriprimed somatic embryos were sown ex vitro. In this study, somatic embryos from interior spruce genotypes 4-2809, 23-2672, and I-1026 were desiccated and stored as described for the first growth regulator study. Prior to nutripriming, genotype I-1026 was imbibed with a matripriming step which consisted of placing the desiccated embryos onto a screen, and then placing the screen on the surface of an agar substrate gelled with 3% phytogel foe 18 hrs. After this imbibition step was completed for genotype I-1026, all three genotypes were nutriprimed for 84 hr in 3% w/v sucrose m24GMD nutripriming solutions and then sown ex vitro into 400-cavity styrofoam miniplug trays filled with peat bound by a polymer (Grow-Tech Inc., San Bautista, Calif.). After sowing was completed, the nutriprimed embryo received exogenous applications of one of the treatments described in Table 8.3.

TABLE 8.3

Plant growth treatments added to horticultural substrates containing ex vitro-sown nutriprimed somatic embryos.

| Treatment # | Growth regulators applied to ex vitro-sown nutriprimed embryos | | |
|---|---|---|---|
| | IBA (μM) | BA (μM) | GA$_{4/7}$ (μM) |
| 1 | 0 | 0 | 0 |
| 2 | 0.2 | 0 | 0 |
| 3 | 0.1 | 0 | 0 |
| 4 | 0.1 | 0.02 | 0 |
| 5 | 0.1 | 0.02 | 0.02 |
| 6 | 0.1 | 0 | 0.1 |
| 7 | HRHT control | | |

After the exogenous application of the plant growth regulator treatments, the blocks were placed onto a non-sterile high-humidity (≧95% RH) germination chamber for one week. Immediately after the trays containing ex vitro sown nutriprimed embryos were placed into the non-sterile high-humidity germination chamber, they were misted with m24GMD solution containing 3% w/v sucrose until the surfaces of the non-sterile growing substrates were well-wetted, and then at daily intervals for a period of 7 days. After the initial 7-day period in the non-sterile high-humidity germination environment, the trays were moved to a non-sterile misting chamber (RH ranged between 75–90%) for two more weeks of growth under an 18-hour photoperiod of 120–150 mol m$^{-2}$s$^{-1}$ PAR with day-night temperatures of 18–23° C. Daily applications of the m24GMD nutrient solution containing 3% w/v sucrose were misted onto the germinants through to the end of the two-week period in the misting chamber. Aseptic techniques or conditions were not used for application of the nutrient solutions, nor for the germination and growing environments during the 3-week culture period.

At the end of the three-week germination period, all survived germinants were counted and examined for root initiation. Germination and rooting percentages were calculated based on total number of embryos sown in each replicate.

The results for this study are recorded in Table 8.4. As in the previous study, exogenous applications of plant growth regulators to nutriprimed interior spruce somatic embryos from genotype 4-2809 did not improve germination or rooting performance. However, exogenous application of IBA alone or in combination with 0.02 uM Ba significantly enhanced germination performance.

TABLE 8.4

Effects of plant growth regulators added to the horticultural growing substrate on ex vitro germination and development of nutriprimed interior spruce somatic embryos.

| Genotype | Dessication treatment | Nutririming treatment | Growth regulator level in nutripriming solutions | | | Germination % | Rooting % |
|---|---|---|---|---|---|---|---|
| | | | IBA (μM) | BA (μM) | GA$_{4/7}$ (μM) | | |
| 4-2809 | HRHT | Control | 0 | 0 | 0 | 32.5 ± 2.5 | 7.5 ± 2.5 |
| 4-2809 | HRHT | Primed | 0 | 0 | 0 | 96.3 ± 2.4 | 81.3 ± 3.1 |
| 4-2809 | HRHT | Primed | 0.2 | 0 | 0 | 97.5 ± 1.4 | 78.8 ± 7.5 |
| 4-2809 | HRHT | Primed | 0.1 | 0 | 0 | 92.5 ± 7.5 | 75.0 ± 10.2 |
| 4-2809 | HRHT | Primed | 0.1 | 0.02 | 0 | 95.0 ± 3.5 | 73.8 ± 3.1 |
| 4-2809 | HRHT | Primed | 0.1 | 0.02 | 0.2 | 90.0 ± 5.4 | 72.5 ± 8.5 |
| 4-2809 | HRHT | Primed | 0.1 | 0 | 0.1 | 83.8 ± 2.4 | 61.3 ± 10.5 |
| 23-2672 | HRHT | Control | 0 | 0 | 0 | 57.5 ± 7.5 | 40.0 ± 10.0 |
| 23-2672 | HRHT | Primed | 0 | 0 | 0 | 76.7 ± 9.4 | 64.8 ± 7.9 |
| 23-2672 | HRHT | Primed | 0.2 | 0 | 0 | 72.5 ± 10.9 | 67.5 ± 10.1 |
| 23-2672 | HRHT | Primed | 0.1 | 0 | 0 | 72.5 ± 11. | 61.3 ± 13.4 |
| 23-2672 | HRHT | Primed | 0.1 | 0.02 | 0 | 74.8 ± 5.5 | 64.8 ± 4.8 |
| 23-2672 | HRHT | Primed | 0.1 | 0.02 | 0.2 | 76.3 ± 9.4 | 68.8 ± 8.0 |
| 23-2672 | HRHT | Primed | 0.1 | 0 | 0.1 | 58.3 ± 8.5 | 48.8 ± 5.2 |
| I-1026 | 85% & frozen | Control | 0 | 0 | 0 | 87.5 ± 2.5 | 47.5 ± 7.5 |
| I-1026 | 85% & frozen | Primed | 0 | 0 | 0 | 78.8 ± 3.8 | 68.8 ± 5.2 |
| I-1026 | 85% & frozen | Primed | 0.2 | 0 | 0 | 80.0 ± 6.8 | 65.0 ± 5.4 |
| I-1026 | 85% & frozen | Primed | 0.1 | 0 | 0 | 91.3 ± 5.5 | 66.3 ± 3.7 |
| I-1026 | 85% & frozen | Primed | 0.1 | 0.02 | 0 | 83.8 ± 5.5 | 71.3 ± 5.5 |
| I-1026 | 85% & frozen | Primed | 0.1 | 0.02 | 0.2 | 82.5 ± 2.5 | 63.8 ± 4.7 |
| I-1026 | 85% & frozen | Primed | 0.1 | 0 | 0.1 | 82.5 ± 6.0 | 67.5 ± 4.3 |

These examples demonstrate that additions of selected plant growth regulators to nutripriming solutions or alternatively, exogenous applications to ex vitro-sown nutriprimed somatic embryos can significantly improve the germination and rooting of somatic embryos. Those skilled in the art will be able to use this information disclosed herein to determine which plant growth regulators, alone or in combination, and at what rates, can be used to enhance the ex vitro germination and development of somatic embryos of their preferred species.

EXAMPLE 9

The objectives for these studies were to determine the effects of environmental conditions during the nutripriming step on the subsequent ex vitro germination and growth of nutriprimed somatic embryos.

The first study assessed the effects of light and temperature conditions during nutripriming on subsequent germination and development performance. Mature somatic embryos of interior spruce (*Picea glauca* (Moench) Voss x *P. engelmannii* Parry ex Engelm.) genotype 23-2672 were desiccated with the HRHT treatment, and then divided into five groups of 160 somatic embryos per group. One group was not primed and served as the HRHT control treatment for this study. The remaining four groups were randomly assigned for nutripriming in 250-ml flasks containing 3% w/v sucrose m24GMD nutrient solutions. The nutripriming step was performed at 5° C. temperature with or without light, or at ambient temperature (i.e., 20–23° C.) conditions with or without light. When light was applied during the nutripriming process, the photoperiod was 24 hours of 30 $\mu$mol m$^{-2}$s$^{-1}$ photosynthetic photon flux. The dark treatment was done by wrapping the flasks with aluminum foil. The duration of each nutripriming treatment was 72 hours.

After the nutripriming step was completed, each treatment was divided into eight groups of twenty embryos and sown by hand on vermiculite media in Sigma polycarbonate boxes. The liquid media in these germination boxes were m24GMD with or without 3% w/v sucrose. Four of the eight groups were sown on media without sucrose while the remaining four groups were sown on media containing 3% w/v sucrose. The experiment design was a random complete block design for each media type. The germination boxes were placed in a germination room and grown for two weeks under 50–70 $\mu$mol m$^{-2}$s$^{-1}$ photosynthetic photon flux of 16-hour photoperiod at an air temperature of 23° C. The germinants were then harvested and assessed for germination rates, hyperhydricity rates, shoot and root length. Germination was defined as germinants having a root longer than 2 mm, and elongated hypercotyl. Hyperhydricity was defined by the thickening of hypercotyl and watery appearance of the germinants, whether germinated or not germinated. The results for this study are summarized in Tables 9.1 and 9.2. Temperatures at which nutripriming was performed did not affect the subsequent germination and development of nutriprimed somatic if 3% w/v sucrose was added to the nutripriming solutions. However, in the absence of 3% w/v sucrose in the nutripriming solutions, only those embryos which were nutriprimed at ambient temperatures germinated successfully. However, the root development of somatic embryos nutriprimed in solutions without sucrose, was significantly reduced when compared to those nutriprimed in solutions containing sucrose. In conclusion, nutripriming can be performed under refrigerated conditions (e.g., 4° C.) if so desired, if sucrose is included as a component of the nutripriming solution.

TABLE 9.1

Effects of temperature and light during nutripriming on germination of interior spruce somatic embryos.

| Nutripriming treatment | | Germination media | | | |
|---|---|---|---|---|---|
| | | m24GMD plus 3% sucrose | | m24GMD | |
| | | Germ-ination % | % with hyperhydricity | Germination % | % with hyperhydricity |
| 5° C. | Dark | 100 | 0 | 0 | 46.3 ± 26.9 |
| | Light | 100 | 2.4 ± 1.4 | 3.8 ± 2.4 | 47.5 ± 27.5 |

TABLE 9.1-continued

Effects of temperature and light during nutripriming on germination of interior spruce somatic embryos.

| Nutripriming treatment | | Germination media | | | |
|---|---|---|---|---|---|
| | | m24GMD plus 3% sucrose | | m24GMD | |
| | | Germ-ination % | % with hyperhydricity | Germination % | % with hyperhydricity |
| 20– 23° C. | Dark | 100 | 2.5 ± 2.5 | 100 | 42.5 ± 24.6 |
| | Light | 100 | 2.4 ± 1.4 | 91.7 ± 8.3 | 40.0 ± 23.2 |
| HRHT control | | 93.8 ± 4.7 | 0 | 25.0 ± 2.5 | 10.0 ± 4.1 |

TABLE 9.2

Effects of temperature and light during nutripriming on growth and development of interior spruce somatic embryos.

| Nutripriming treatment | | Germination media | | | |
|---|---|---|---|---|---|
| | | m24GMD plus 3% sucrose | | m24GMD | |
| | | Shoot length (mm) | Root length (mm) | Shoot length (mm) | Root length (mm) |
| 5° C. | Dark | 15.9 ± 0.4 | 12.5 ± 0.8 | 0 | 0 |
| | Light | 15.8 ± 0.4 | 12.9 ± 0.7 | 11.4 ± 0.3 | 1.5 ± 0.1 |
| 20–23° C. | Dark | 17.4 ± 0.4 | 12.4 ± 0.8 | 12.7 ± 0.3 | 2.9 ± 0.1 |
| | Light | 18.1 ± 0.4 | 11.6 ± 0.9 | 14.7 ± 0.3 | 2.4 ± 0.1 |
| HRHT control | | 15.3 ± 0.4 | 11.2 ± 0.7 | 10.9 ± 0.5 | 0.2 ± 0.1 |

The second study assessed the effects adding various osmotica to nutripriming solutions on subsequent germination and development performance. Mature somatic embryos of interior spruce (*Picea glauca* (Moench) Voss x *P. engelmannii* Parry ex Engelm.) genotype 23-2672 were desiccated with the HRHT treatment, and then divided into 10 groups of 160 somatic embryos per group. One group was not primed and served as the HRHT control treatment for this study. The remaining nine groups were randomly assigned to one of the following osmoticant treatments added to the m24GMD nutripriming solution: 1% w/v betaine, 1.65% w/v fructose, 1.65% w/v glucose, 1.65% w/v mannitol, 1.65% w/v sorbitol, 3% w/v lactose, 3% w/v maltose, 3% w/v sucrose or 10% w/v polyethylene glycol (PEG) 4000. The final osmotic potential in all treatments was of −0.35 MPa except for the PEG solution, which had an osmotic potential of −0.32 MPa. The nutripriming solutions and embryos were placed into 250-ml Kimax® baffled flasks. The nutripriming duration was 72 hrs at temperatures ranging between 20–23° C., and a 24-hr photoperiod of 30 $\mu$mol m$^{-2}$s$^{-1}$ photosynthetic photon flux.

At the completion of the nutripriming step, the nutriprimed embryos from each treatment were divided into 8 groups of 20 embryos and sown by hand onto vermiculite media in Sigma polycarbonate boxes. The liquid media in these germination boxes were either 3% w/v sucrose m24GMD or m24GMD without sucrose. The experiment design was a random complete block design for each media type. Each nutripriming treatment had 4 replicates of 20 embryos in each germination media type. The germination boxes were placed in a germination room and grown for two weeks under 50–70 μmol m$^{-2}$s$^{-1}$ photosynthetic photon flux of 16-hour photoperiod at an air temperature of 23° C. The germinants were then harvested and assessed for germination rates, hyperhydricity rates, shoot and root length. Germination was defined as germinants having a root longer than 2 mm, and elongated hypercotyl. Hyperhydricity was defined by the thickening of hypercotyl and watery appearance of the germinants, whether germinated or not germinated. The results for this study are summarized in Tables 9.3 and 9.4.

In summary, although addition of osmoticants to nutripriming solutions containing 3% w/v sucrose did not adversely affect germination percentage, all osmoticant treatments with the exception of betain, mannitol and lactose caused increased levels of hyperhydricity. When the osmoticants were added to nutripriming solutions which did not contain sucrose, germination performance became variable and high levels of hyperhydricity were observed (Table 9.3). Nutriprimed embryos from all osmoticant treatments formed roots and shoots, but the best performance was observed in embryos nutriprimed in 3% w/v sucrose m24GMD nutripriming solution that did not contain any osmoticants (Table 9.4).

TABLE 9.3

Effects of osmoticants on germination of nutriprimed interior spruce somatic embryos.

| | Germination media | | | |
|---|---|---|---|---|
| | m24GMD plus 3% sucrose | | m24GMD | |
| Osmoticant added to nutripriming solution | Germination % | % with hyperhydricity | Germination % | % with hyperhydricity |
| 1% betaine | 100 | 2.5 ± 2.5 | 45.0 ± 26.3 | 76.3 ± 19.1 |
| 1.65% fructose | 100 | 16.3 ± 9.4 | 87.5 ± 7.8 | 86.3 ± 9.4 |
| 1.65% glucose | 96.3 ± 2.4 | 18.2 ± 6.9 | 96.2 ± 2.4 | 58.8 ± 8.0 |
| 1.65% mannitol | 100 | 4.7 ± 3.2 | 24.6 ± 12.7 | 93.5 ± 5.0 |
| 1.65% sorbitol | 100 | 7.5 ± 2.5 | 5.0 ± 5.0 | 92.6 ± 6.0 |
| 3% lactose | 100 | 3.7 ± 2.4 | 27.6 ± 24.3 | 100 |
| 3% maltose | 98.8 ± 1.3 | 17.5 ± 7.8 | 0 | 100 |
| 3% sucrose | 100 | 2.4 ± 1.4 | 91.7 ± 8.3 | 40.0 ± 23.2 |
| 10% PEG 4000 | 100 | 6.0 ± 6.0 | 6.3 ± 6.3 | 97.5 ± 4.3 |
| HRHT control | 93.8 ± 4.7 | 0 | 25.0 ± 25.0 | 10.0 ± 4.1 |

TABLE 9.4

Effects of osmoticants on the development of nutriprimed interior spruce somatic germinants.

| | Germination media | | | |
|---|---|---|---|---|
| | m24GMD plus 3% sucrose | | m24GMD | |
| Osmoticant added to nutripriming solution | Shoot length (mm) | Root length (mm) | Shoot length (mm) | Root length (mm) |
| 1% betaine | 14.2 ± 0.3 | 12.2 ± 0.8 | 11.2 ± 0.3 | 0.4 ± 0.2 |
| 1.65% fructose | 13.5 ± 0.3 | 12.2 ± 0.8 | 10.0 ± 0.3 | 2.1 ± 0.1 |
| 1.65% glucose | 14.8 ± 0.4 | 10.8 ± 0.8 | 10.8 ± 0.3 | 1.7 ± 0.2 |
| 1.65% mannitol | 13.6 ± 0.3 | 12.0 ± 0.5 | 10.0 ± 0.3 | 0.3 ± 0.1 |
| 1.65% sorbitol | 14.5 ± 0.4 | 15.5 ± 1.0 | 10.7 ± 0.3 | 0.4 ± 0.1 |
| 3% lactose | 15.5 ± 0.3 | 12.4 ± 0.8 | 11.5 ± 0.2 | 0.3 ± 0.1 |
| 3% maltose | 14.2 ± 0.3 | 11.5 ± 0.8 | 11.2 ± 0.3 | 0.8 ± 0.1 |
| 3% w/v sucrose | 18.1 ± 0.4 | 11.6 ± 0.9 | 14.7 ± 0.3 | 2.4 ± 0.1 |
| 10% PEG 4000 | 14.8 ± 0.3 | 12.2 ± 1.1 | 10.8 ± 0.3 | 0.3 ± 0.1 |
| HRHT control | 13.2 ± 0.5 | 12.6 ± 1.2 | 10.9 ± 0.5 | 0.2 ± 0.1 |

EXAMPLE 10

The objective of this study was to assess the effects of nutripriming on the development of nutrient reserves within somatic embryos of interior spruce.

Mature somatic embryos of interior spruce (*Picea glauca* (Moench) Voss x *P. engelmannii* Parry ex Engelm.) genotype I-1026 were desiccated with the HRHT treatment.

Nine groups of 20 embryos were randomly picked up from the post-HRHT population. The length of each embryo was measured. Subsequently, four groups of embryos were nutriprimed in m24GMD solutions containing 2% w/v sucrose for durations of 1,2,3 or 4 days. The remaining 4 groups of embryos were nutriprimed in m24GMD solutions containing 4% w/v sucrose for durations of 1,2,3 or 4 days. At the conclusion of each nutripriming treatment, embryos were collected on 53-μ nylon mesh and rinsed three times with deionized water. The embryos were then blotted dry with filter paper and their post-nutripriming lengths measured. Each group was then divided into 5 sets of 4 embryos and were placed in tared microcentrifugel tubes. After fresh weight determinations, the embryos were dried at 60° C. for 24 hours and their dry weight determined. The ninth group, which consisted of non-nutriprimed post-HRHT embryos (i.e., the controls), was also divided into 5 sets of 4 embryos for determinations of length, fresh and dry weights.

An additional 8 groups of 160 embryos per group were sorted from the post-HRHT treated embryos. Four groups of embryos were nutriprimed in m24GMD solutions containing 2% w/v sucrose for durations of 1,2,3 or 4 days. The remaining 4 groups of embryos were nutriprimed in m24GMD solutions containing 4% w/v sucrose for durations of 1,2,3 or 4 days. At the conclusion of each nutripriming treatment, embryos were collected on 53-μ nylon mesh and rinsed three times with deionized water. The embryos were then blotted dry with filter paper. Each group was then randomly divided into 16 samples of 15 embryos. One sample was placed in a tared 1.5-ml microcentrifugel tube and weighed for fresh weight. The tubes were then dropped in liquid $N_2$ for 10 min and stored at −80° C. until biochemical analyses could be done as outlined below.

Determination of Triacylglyceride Contents

The protocols for extraction, purification, and assay of triacylglyceride (TAG) followed the procedures of Feirer et al. (1989). Briefly, samples of (a) 15 nutriprimed or, (b) 15 non-nutriprimed somatic embryos, or (c) 10 zygotic embryos which were dissected from dry seeds from each of three seedlots (SL#s 28840; 60245; 08729) were ground for 2 minutes in a 1.5-ml microcentrifugel tube with 50 mg of aluminum oxide (Sigma, Activity Grade I) and 0.1 ml of anhydrous isopropanol (Fisher, HPLC grade) using a motorized pestle. The pestle was washed three times with 0.3 ml of isopropanol. The washing solutions were collected in the microcentrifugel tube. The tubes were then placed on a shaker (150 rpm) for 15 minutes, followed by 15 minutes centrifugation at 13,000 rpm.

To purify the lipid extracts, a 0.8-ml aliquot of supernatant was withdrawn from each sample and added into a 10-ml test tube containing 0.8 g of aluminum oxide and 1.8 ml of isopropanol. The tubes were placed on a shaker at 150 rpm for 15 minutes and then centrifuged at 3,000 rpm for 20 minutes. The supernatant was transferred to a new tube. The pellet was resuspended in 2.6 ml of isopropanol. The tubes were again placed on the shaker, resuspended and re-centrifuged. The resultant supernatant was pooled with the initial supernatent collected from the sample. To quantify TAG levels in the purified extracts, an 1-ml aliquot of the pooled supernatant was withdrawn, placed in a 1.5-l microcentrifugel tube, and recentrifuged at 13,000 rpm for 15 min. A 0.8-ml aliquot of supernatant was withdrawn and placed in a 5-ml polypropylene tube. A 0.2-ml aliquot of 1 N KOH was added to each tube. The tubes were capped, vortexed, and placed in a 60° C. water bath for 5 minutes to enable the following reaction to occur:

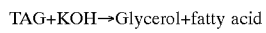
TAG+KOH→Glycerol+fatty acid

After 5-minute reaction period, the tubes were removed from the water bath and cooled in a basin filled with running tap water for 2 minutes. Then, 0.2-ml aliquot of sodium m-periodate was added to each tube to facilitate the following reaction:

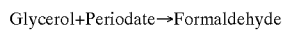
Glycerol+Periodate→Formaldehyde

After a 10-min incubation, 1.2-ml aliquot of color reagent (a mixture of ammonium acetate and acetylacetone in isopropanol) was added to each tube, after which, the tubes were placed in a 60° C. water bath for 30 min to enable the following reaction to take place:

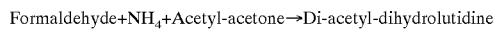
Formaldehyde+$NH_4$+Acetyl-acetone→Di-acetyl-dihydrolutidine

The tubes were then cooled in a basin filled with running tap water for 2 minutes. The absorbance in each solution was determined in a spectrophotometer set at 410 nm.

Results

Nutripriming affected the onset of biological activity within somatic embryos as evidenced by elongation along their embryonyl axes (Table 10.1). Furthermore, as the duration of nutripriming treatments was increased, the magnitude of embryo elongation also increased (Table 10.1). In this study, embryo elongation was more pronounced when nutripriming solutions were amended with 2% w/v sucrose as compared to 4% w/v sucrose. Also, it appeared that the maximal response occurred with 3–4 day nutripriming treatments.

TABLE 10.1

Length (mm) of interior spruce genotype I-1026 somatic embryos before and after nutripriming treatments.

| | | Sucrose level in nutripriming solution | | | |
| | | 2% in m24GMD | | 4% in m24GMD | |
| Duration of nutripriming (days) | Post-HRHT control | Embryo length before nutri-priming | Embryo length after nutri-priming | Embryo length before nutri-priming | Embryo length after nutri-priming |
| --- | --- | --- | --- | --- | --- |
| 0 | 2.6 ± 0.1 | | | | |
| 1 | | 2.1 ± 0.1 | 2.3 ± 0.1 | 2.4 ± 0.1 | 2.5 ± 0.1 |
| 2 | | 2.1 ± 0.1 | 2.6 ± 0.1 | 2.2 ± 0.1 | 2.6 ± 0.1 |
| 3 | | 2.5 ± 0.1 | 3.5 ± 0.1 | 2.1 ± 0.1 | 2.8 ± 0.1 |
| 4 | | 2.6 ± 0.1 | 4.1 ± 0.1 | 2.1 ± 0.1 | 3.2 ± 0.1 |

Furthermore, it was clearly apparent that increasing the duration of the nutripriming periods resulted in significant increases in embryonyl biomass formation as evidenced by increases in dry weights compared to the dry weight HRHT control embryos, of 32–54% after 3 days of nutripriming, and 65–75% after 4 days of nutripriming (Table 10.2).

TABLE 10.2

Effects of nutripriming on dry weights (mg) of interior spruce genotype I-1026 somatic embryos (means of 200 embryos).

| Embryo treatment | Duration of nutri-priming (days) | Initial dry weight of embryos | Dry weight of embryos after nutripriming in | |
| | | | 2% w/v sucrose m24GMD | 4% sucrose m24GMD |
| --- | --- | --- | --- | --- |
| HRHT control | — | 0.281 ± 0.010 | | |
| Nutriprimed | | | | |
| | 1 | | 0.240 ± 0.010 | 0.296 ± 0.009 |
| | 2 | | 0.314 ± 0.011 | 0.342 ± 0.013 |
| | 3 | | 0.373 ± 0.020 | 0.434 ± 0.014 |
| | 4 | | 0.464 ± 0.027 | 0.491 ± 0.014 |

The concentration of sucrose in nutripriming solutions and the duration of nutripriming significantly affected the accumulation of storage reserve lipids, i.e., TAGs, in interior spruce somatic embryos (Table 10.3). While TAG levels increased over 90% in embyos nutriprimed for one day in solutions containing 2% w/v sucrose, the TAG levels subsequently declined as the duration nutripriming was increased, to the point where by the fourth day of nutripriming, the TAG levels were only 10% greater than in the non-nutriprimed controls. On the other hand, the TAG levels in somatic embryos nutriprimed in solutions containing 4% w/v sucrose doubled within the first day and remained at that level through the fourth day of nutripriming. Furthermore, it should be noted that although the TAG levels in the HRHT control somatic embryos were comparable to those in zygotic embryos, embryos nutriprimed in solutions containing 4% w/v sucrose contained 85% more TAG than were present in the zygotic embryos.

TABLE 10.3

Comparison of lipid levels in interior spruce zygotic embryos with control and nutriprimed somatic embryos of genotype I-1026

| Embryo source | Nutripriming treatment | Priming duration (days) | Lipid content ($\mu$g/embryo) |
|---|---|---|---|
| Zygotic seed lot# | | | |
| 28840 | | | 52.3 ± 5.8 |
| 60245 | | | 68.7 ± 2.9 |
| 08729 | | | 65.8 ± 4.3 |
| Somatic genotype I-1026 | HRHT control | | 55.6 ± 5.7 |
| Somatic genotype I-1026 | 2% sucrose in m24GMD | 1 | 107.6 ± 12.1 |
| | | 2 | 112.2 ± 11.1 |
| | | 3 | 64.1 ± 5.6 |
| | | 4 | 63.0 ± 2.7 |
| Somatic genotype I-1026 | 4% sucrose in m24GMD | 1 | 113.9 ± 17.1 |
| | | 2 | 112.9 ± 10.1 |
| | | 3 | 113.8 ± 11.8 |
| | | 4 | 113.2 ± 14.6 |

These results clearly demonstrate that nutripriming somatic embryos in solutions containing sucrose and mineral nutrients facilitates and enhances the physiological and biochemical processes associated with the post-imbibition events that occur in Phase 2 of germination. Furthermore, it is evident that nutripriming enables somatic embryos to accumulate storage reserve lipids which enhance the later events associated with completion of germination and the onset of seedling growth and development.

EXAMPLE 11

The objective of this study was to examine the effects of nutripriming duration, post-nutripriming desiccation, and post-desiccation storage on ex vitro germination of interior spruce somatic embryos in non-sterile substrates and environments.

Mature somatic embryos of interior spruce (*Picea glauca* (Moench) Voss x *P. engelmannii* Parry ex Engelm.) genotypes 4-2809 and I-1026 were desiccated with the HRHT treatment and stored at 4° C. Embryos were nutriprimed for one of 1, 2, or 3 days in ½ m24GMD liquid medium containing 3% w/v sucrose in 250-ml Kimax® baffled Erlenmeyer culture flasks as described in previous examples.

Embryos nutriprimed from each treatment, along with post-HRHT controls, were divided into groups of 155 embryos. Each group was placed on an 800-$\mu$m nylon screen in a 6-cm Petri dish and randomly assigned to one of two desiccation treatments. Desiccation treatment #1 was 90.0% RH (embryos desiccated over a 2.83-mol NaCl solution) while desiccation treatment #2 was 85.0% RH (embryos desiccated over saturated KCl solutions). Both desiccation treatments were carried out in sealed chambers at 20° C. for 3 days. Each "nutripriming period X desiccation" treatment combination for each genotype had 3 groups that were desiccated in three chambers. At the end of each desiccation treatment, 1 sample of 5 embryos was taken from each chamber for measurement of water content based on differences in fresh and oven-dry weights (3 days @65° C.) weight. One group was immediately imbibed using a matripriming process on semi-solid substrate comprised of 0.6% agar, 3% w/v sucrose, and ½ m24GMD germination medium in 10-cm Petri dishes for 68 hours at 23° C. in a Conviron tissue culture chamber (Conviron Ltd., Winnipeg, Mass.). The imbibed embryos were then sown either in vitro or ex vitro as described below.

The other two groups of embryos were scraped off the nylon screens into sterilized 2.0-ml polypropylene, low-temperature freezer vials (VWR Canlab, Mississauga, ON). The vials were capped. One group was stored at −20° C. in a freezer and the other group was stored at 4.0° C. After one week of storage, the desiccated nutriprimed embryos were imbibed with the matripriming process described previously, then germinated in vitro or ex vitro. At each sowing time, there were un-desiccated controls which received similar HRHT or priming treatments to the desiccated nutriprimed embryos.

In vitro germination was on the same medium as described for imbibition, i.e., on a semi-solid substrate comprised of 0.6% agar, 3% w/v sucrose, and ½m24GMD germination medium in 10-cm Petri dishes. Each "genotype X nutripriming duration X desiccation" treatment combination had 3 replicates of 10 embryos in a 10-0 cm Petri dish. Germination proceeded under sterile conditions in an environment-controlled tissue culture room.

Ex vitro germination was conducted in a peat-based polymer-bound soilless mix dispensed into 504-cell (4 ml/cell) Styrofoam miniplug trays (Grow-Tech Inc., San Bautista, Calif.). The ex vitro experiment had 3 replicates of 20 embryos for each treatment combination.

The sown trays were placed in a conventional non-sterile horticulture germination chamber in an environment-controlled growth room. The environmental conditions were 22–24° C. air temperature, 80–100% RH, 0.10–0.15% $CO_2$, and a 16-hr photoperiod with 40–120 $\mu$mol $m^{-2}s^{-1}$ photosynthetic photon flux. Immediately after the trays containing ex vitro sown nutriprimed embryos were placed into the non-sterile germination chamber, they were misted with a 3% w/v sucrose solution until the surfaces of the non-sterile growing substrates were well-wetted. Subsequently, the trays were misted with the 3% w/v sucrose solution daily for a 2-week germination period. Mineral nutrients in the form of a plant-starter fertilizer solution at a rate of 1 g $l^{-1}$ of 11-41-8 N-P-K (Plant Products Co. Ltd., Brampton, ON) were misted onto the germinating embryos at 2-day intervals. Aseptic techniques or conditions were not used for application of the nutrient solutions, nor for the germination environment during the 2-week culture period. Furthermore, prophylactic applications of 0.1 g/l benlate, 0.05 g/l ampicillin plus 0.05 g/l penicillin G (or 0.1 ampicillin), and 5 ml/l Gnatrol were applied at 5-day intervals to control fungi, bacteria, and fungus fly larvae.

The data in Table 11.1 indicate that a greater degree of desiccation occurred with nutriprimed embryos when they were desiccated in environments with RH values of 85% compared to desiccation environments with 90% RH.

TABLE 11.1

Water content (based on fresh and dry weight) of embryos at the end of desiccation treatment before being imbibed for germination or placed in low temperature storage.

| Interior spruce genotype | Nutri-priming Duration (days) | Desiccation treatment (% RH) | Water content (% fresh weight) | Water content (% dry weight) |
|---|---|---|---|---|
| 4–2809 | HRHT control | 85 | 11.47 ± 0.68 | 12.97 ± 0.87 |
|  |  | 90 | 11.44 ± 1.55 | 12.98 ± 1.98 |
|  | 1 | 85 | 17.52 ± 2.72 | 21.50 ± 4.02 |
|  |  | 90 | 22.10 ± 1.73 | 28.50 ± 2.82 |
|  | 2 | 85 | 25.15 ± 6.69 | 35.98 ± 13.34 |
|  |  | 90 | 20.61 ± 1.73 | 26.08 ± 2.81 |
|  | 3 | 85 | 22.00 ± 2.01 | 28.38 ± 3.23 |
|  |  | 90 | 31.59 ± 2.17 | 46.50 ± 4.80 |
| I-1026 | HRHT control | 85 | 17.36 ± 2.93 | 21.33 ± 4.47 |
|  |  | 90 | 19.75 ± 1.54 | 24.71 ± 2.36 |
|  | 1 | 85 | 16.06 ± 0.35 | 19.14 ± 0.49 |
|  |  | 90* | — | — |
|  | 2 | 85 | 20.36 ± 0.46 | 25.57 ± 0.73 |
|  |  | 90 | 40.34 ± 5.80 | 71.12 ± 18.05 |
|  | 3 | 85 | 22.49 ± 0.51 | 29.03 ± 0.85 |
|  |  | 90 | 51.65 ± 0.65 | 106.88 ± 2.77 |

*Salt solutions inadvertantly saturated at least one of the three replicates in this treatment. Consequently, the results for this treatment were compromised.

The data in Table 11.2 demonstrate that somatic embryos can be desiccated and stored after nutripriming treatments are completed, without significant losses in germination vigour or subsequent seedling growth and development. The data also demonstrate that desiccated nutriprimed somatic embryos can be stored under a wide range of temperature conditions ranging from ambient (i.e., 23° C.) to refrigerated (i.e., 4° C.), and frozen storage (i.e, −20° C.). We surprisingly found that embryos desiccated after 3 days of nutripriming in solutions containing 3% w/v surcose, and stored at ambient temperatures maintained 100% germination vigour and conversion into fully intact seedlings when sown ex vitro and germinated in non-sterile growing media cultured in non-sterile environmental conditions, while those stored at −20° C. demonstrated 93% germination success and 80% conversion into fully intact seedlings when sown and germinated in the same non-sterile environments.

TABLE 11.2

Effects of desiccation treatment and storage conditions on subsequent germination and growth of nutriprimed somatic embryos.

| Duration of priming (days) | Desiccation treatment (% RH) | Storage Temp (° C.) | Germination % | Rooting % |
|---|---|---|---|---|
| HRHT control | Control 1 | 23 | 100 | 100 |
|  | Control 2 | 23 | 100 | 96.7 ± 3.3 |
|  | 85 | 23 | 100 | 75.0 ± 8.3 |
|  |  | 4 | 100 | 100 |
|  |  | −20 | 100 | 100 |
|  | 90 | 23 | 100 | 100 |
|  |  | 4 | 100 | 100 |
|  |  | −20 | 70.0 ± 20.0 | 55.0 ± 5.0 |
| 1 | Control 1 | 23 | 96.7 ± 3.3 | 80.0 ± 5.8 |
|  | Control 2 | 23 | 100 | 96.7 ± 3.3 |
|  | 85 | 23 | 96.7 ± 3.3 | 66.7 ± 14.5 |
|  |  | 4 | 96.7 ± 3.3 | 36.7 ± 14.5 |
|  |  | −20 | 100 | 56.7 ± 3.3 |
|  | 90 | 23 | 100 | 96.7 ± 3.3 |
|  |  | 4 | 100 | 93.3 ± 3.3 |
|  |  | −20 | 100 | 100.0 ± 0.0 |
| 2 | Control 1 | 23 | 100 | 93.3 ± 3.3 |
|  | Control 2 | 23 | 100 | 100.0 ± 0.0 |
|  | 85 | 23 | 96.7 ± 3.3 | 86.7 ± 8.8 |
|  |  | 4 | 96.7 ± 3.3 | 60.0 ± 10.0 |
|  |  | −20 | 100 | 76.7 ± 6.7 |
|  | 90 | 23 | 100 | 96.7 ± 3.3 |
|  |  | 4 | 96.7 ± 3.3 | 70.0 ± 5.8 |
|  |  | −20 | 100 | 93.3 ± 6.7 |
| 3 | Control 1 | 23 | 100 | 100 |
|  | Control 2 | 23 | 100 | 100 |
|  | 85 | 23 | 96.7 ± 3.3 | 73.3 ± 8.8 |
|  |  | 4 | 76.7 ± 18.6 | 33.3 ± 8.8 |
|  |  | −20 | 95.0 ± 5.0 | 55.0 ± 35.0 |
|  | 90 | 23 | 100 | 100 |
|  |  | 4 | 46.7 ± 3.3 | 33.3 ± 6.7 |
|  |  | −20 | 93.3 ± 6.7 | 80.0 ± 5.8 |

EXAMPLE 12

The objective for this study was to assess the effects of: (a) elevated sucrose levels in nutripriming solutions, and (b) extended nutripriming durations on the germination performance os somatic embryos.

Mature somatic embryos of interior spruce (*Picea glauca* (Moench) Voss x *P. engelmannii* Parry ex Engelm.) genotypes 5-1378 and 107-2049 t were desiccated with the HRHT treatment and stored at 4° C. Embryos were subsequently removed from storage and nutriprimed for one of 3, 4, or 5 days periods as previously described in ½ m24GMD liquid medium containing one of the following sucrose concentrations; 4, 6, 8, and 10% (all w/v). After the nutripriming treatments were completed, the embryos were sown ex vitro onto a peat-based polymer-bound horticultural growing substrate in 504-cell (4 ml/cell) styrofoam miniplug trays (Grow-Tech Inc., San Bautista, Calif.). The sown trays were then placed into a conventional non-sterile horticulture germination chamber in an environment-controlled growth room. The environmental conditions were 22–24° C. air temperature, 80–100% RH, 0.10–0.15% $CO_2$, and a 16-hr photoperiod with 40–120 $\mu$mol $m^{-2}s^{-1}$ photosynthetic photon flux. Immediately after the trays containing ex vitro sown nutriprimed embryos were placed into the non-sterile germination chamber, they were misted with a ½ m24GMD nutrient solution amended with 3% w/v sucrose solution until the surfaces of the non-sterile growing substrates were well-wetted. Subsequently, the trays were misted with this solution daily for a 3-week germination period. Aseptic techniques or conditions were not used for application of the nutrient solutions, nor for the germination environment during the 2-week culture period. Furthermore, prophylactic applications of 0.1 g/l benlate, 0.05 g/l ampicillin plus 0.05 g/l penicillin G (or 0.1 ampicillin), and 5 ml/l Gnatrol® were applied at 5-day intervals to control fungi, bacteria, and fungus fly larvae.

The data in Tables 12.1 and 12.2 demonstrate that the range of sucrose concentrations that can be used for nutripriming somatic embryos can extend up to at least 10% and also, that the duration of nutripriming can be increased to at least 5 days.

TABLE 12.1

Effects of increased sucrose concentrations and extended nutripriming duration on subsequent ex vitro germination and growth of somatic embryos from interior spruce genotype 5–1378.

| % sucrose in nutripriming solutions | Duration of priming (days) | Germination % | Rooting % |
|---|---|---|---|
| 3 | 3 | 83.3 ± 8.8 | 73.3 ± 8.8 |
| 4 | 3 | 98.3 ± 1.7 | 86.7 ± 7.3 |
|   | 4 | 96.7 ± 3.3 | 91.7 ± 4.4 |
|   | 5 | 96.5 ± 1.8 | 91.5 ± 6.0 |
| 6 | 3 | 91.7 ± 4.4 | 86.7 ± 3.3 |
|   | 4 | 96.7 ± 3.3 | 90.0 ± 2.9 |
|   | 5 | 98.3 ± 1.7 | 88.3 ± 4.4 |
| 8 | 3 | 91.7 ± 4.4 | 66.7 ± 12.0 |
|   | 4 | 100 | 91.7 ± 3.3 |
|   | 5 | 95.0 ± 5.0 | 86.7 ± 8.3 |
| 10 | 3 | 84.7 ± 2.9 | 52.5 ± 7.2 |
|   | 4 | 100 | 88.3 ± 6.0 |
|   | 5 | 98.3 ± 1.7 | 91.7 ± 4.4 |

TABLE 12.2

Effects of increased sucrose concentrations and extended nutripriming duration on subsequent ex vitro germination and growth of somatic embryos from interior spruce genotype 107–2049.

| % sucrose in nutripriming solutions | Duration of priming (days) | Germination % | Rooting % |
|---|---|---|---|
| 3 | 3 | 91.7 ± 4.4 | 68.3 ± 6.0 |
| 4 | 3 | 90.0 ± 5.0 | 71.7 ± 8.8 |
|   | 4 | 84.6 ± 6.2 | 62.3 ± 13.0 |
|   | 5 | 93.3 ± 6.7 | 76.2 ± 4.5 |
| 6 | 3 | 81.7 ± 3.3 | 66.7 ± 3.3 |
|   | 4 | 85.8 ± 2.2 | 69.6 ± 6.1 |
|   | 5 | 86.7 ± 3.3 | 70.0 ± 0.0 |
| 8 | 3 | 76.7 ± 4.4 | 51.7 ± 4.4 |
|   | 4 | 93.3 ± 4.4 | 88.3 ± 4.4 |
|   | 5 | 93.3 ± 4.4 | 60.0 ± 0.0 |
| 10 | 3 | 81.7 ± 6.7 | 36.7 ± 10.1 |
|   | 4 | 90.0 ± 7.6 | 76.7 ± 8.3 |
|   | 5 | 86.7 ± 1.7 | 51.7 ± 12.0 |

EXAMPLE 13

The objective of this study was to assess the effects of nutripriming on the germination of an angiosperm plant species, *Brassica napus*.

Un-dessicated somatic embryos of canola cultivar Topas (*Brassica napus* cv. Topas) were nutriprimed in 250-ml baffled Erlenmeyer culture flasks containing ½ m24GMD liquid medium supplemented with 3% w/v sucrose plus 80 unit $ml^{-1}$ penicillin G, for a period of 7 days on a shaker table (80 rpm) in a controlled environment room kept at a temperature ranging between 20–23° C. and with a photoperiod of 20–40 $\mu mol\ m^{-2}s^{-1}$ photosynthetic photon flux. After completion of the nutripriming step, the nutriprimed canola embryos were sown ex vitro onto 400-cavity styrofoam miniplug trays filled with peat bound by a polymer (Grow-Tech Inc., San Bautista, Calif.). After sowing, the trays were placed into a non-sterile high-humidity ($\geq 95\%$ RH) germination chamber for one week. In both studies, immediately after the trays containing ex vitro sown nutriprimed embryos were placed into the non-sterile high-humidity germination chamber, they were misted with ½ m24GMD nutrient solution amended with 3% w/v sucrose once daily for five days. Thereafter, a 1 g $I^{-1}$ of 11-41-8 fertilizer (Plant Products Co. Ltd., Brampton, ON) solution was applied three times week for the duration of the 3-week germination period. Aseptic techniques or conditions were not used for application of the nutrient solutions, or for the germination and growing environments during the 3-week culture period. At the completion of the 3-week period, 97.3% of the ex vitro sown nutriprimed canola somatic embryos germinated in non-sterile growing mix in a non-sterile growing environment.

Mature somatic embryos of canola cultivar Topas (*Brassica napus* cv. Topas), were desiccated for a 3-week period using the HRHT treatment. After desiccation was completed, the somatic embryos were nutriprimed in 250-ml baffled Erlenmeyer culture flasks containing ½ m24GMD liquid medium supplemented with 3% w/v sucrose plus 80 units $ml^{-1}$ penicillin G, for a period of 7 days on a shaker table (80 rpm) in a controlled environment room kept at a temperature ranging between 20–23° C. and with a photoperiod of 20–40 $\mu mol\ m^{-2}s^{-1}$ photosynthetic photon flux. After completion of the nutripriming step, the nutriprimed canola embryos were sown ex vitro onto 400-cavity styrofoam miniplug trays filled with peat bound by a polymer (Grow-Tech Inc., San Bautista, Calif.). After sowing, the trays were placed into a non-sterile high-humidity ($\geq 95\%$ RH) germination chamber for one week. In both studies, immediately after the trays containing ex vitro sown nutriprimed embryos were placed into the non-sterile high-humidity germination chamber, they were misted with ½ m24GMD nutrient solution amended with 3% w/v sucrose once daily for five days. Thereafter, 1 g $I^{-1}$ of 11-41-8 fertilizer (Plant Products Co. Ltd., Brampton, ON) solution was applied three times a week for the duration of the 3-week germination period. Aseptic techniques or conditions were not used for application of the nutrient solutions, or for the germination and growing environments during the 3-week culture period. At the completion of the 3-week period, 96.5% of the desiccated then nutriprimed, canola somatic embryos germinated when sown ex vitro into a non-sterile growing mix and maintained in a non-sterile growing environment.

Un-dessicated somatic embryos of canola cultivar Topas (*Brassica napus* cv. Topas) were nutriprimed in 250-ml baffled Erlenmeyer culture flasks containing ½ m24GMD liquid medium supplemented with 3% w/v sucrose plus 80 units $ml^{-1}$ penicillin G, for a period of 7 days on a shaker table (80 rpm) in a controlled environment room kept at a temperature ranging between 20–23° C. and with a photoperiod of 20–40 $\mu mol\ m^{-2}s^{-1}$ photosynthetic photon flux. After completion of the 1-week nutripriming step, the nutriprimed canola embryos were desiccated with a 1-week HRHT treatment and then separated into three groups. Group 1 was further desiccated in a 92.4% RH environment, Group 2 was desiccated in an 88.5% RH environment while Group 3 was desiccated in and 85% RH environment. Each group was desiccated for 3 days after which subsamples were removed for moisture content determinations. After the desiccation treatments were completed, the nutriprimed then desiccated canola somatic embryos were sown ex vitro onto 400-cavity styrofoam miniplug trays filled with peat bound by a polymer (Grow-Tech Inc., San Bautista, Calif.). After sowing, the trays were placed into a non-sterile high-humidity ($\geq 95\%$ RH) germination chamber for one week. In both studies, immediately after the trays containing ex vitro sown nutriprimed embryos were placed into the non-sterile high-humidity germination chamber, they were misted with ½ m24GMD nutrient solution amended with 3% w/v sucrose once daily for five days. Thereafter, a 1 g $l^{-1}$ of 11-41-8 fertilizer (Plant Products Co. Ltd., Brampton, ON) solution was applied three times a week for the duration of the 3-week germination period. Aseptic techniques or conditions were not used for application of the nutrient solutions, or for the germination and growing environments during the 3-week culture period. The data recorded in Table 13 demonstrate that nutriprimed canola somatic embryos can be desiccated prior to ex vitro sowing and germination.

TABLE 13

Effects of post-nutripriming desiccation on ex vitro germination of canola somatic embryos.

| Replicate # | Desiccation treatment | Water content (%) | Germination % |
|---|---|---|---|
| 1 | 92.4% RH | 23.2 ± 0.4 | 96.3 |
|   | 88.5% RH | 15.4 ± 0.7 | 62.5 |
|   | 85.0% RH | 13.1 ± 0.4 | 22.2 |
| 3 | 92.4% RH | 20.5 ± 0.5 | 85.7 |
|   | 88.5% RH | 15.5 ± 0.4 | 35.7 |
|   | 85.0% RH | 14.5 ± 0.5 | 26.2 |
| 4[1)] | 92.4% RH | 17.6 ± 0.6 | 76.7 |
|   | 88.5% RH | 13.4 ± 0.1 | 40.0 |
|   | 85.0% RH | 12.7 ± 1.1 | 43.3 |

[1)]Germination percentages were recorded 2 weeks after sowing

REFERENCES

1. Bradford, K. J. (1986) Manipulation of seed water relation via osmotic priming to improve germination under stress conditions. HortScience 21: 1105–1112.
2. Carlson, W. C. and J. E. Hartle. (1995) Manufactured Seeds of Woody Plants. IN Somatic Embryogenesis of Woody Plants. Vol. I. S. M. Jain, P. K. Gupta, and R. J. Newton (Eds.) Kluwer Academic Publishers, Dordrecht, The Netherlands. pp. 253–263.
3. Feirer, R P, Conkey, J. H., Verhagen, S. A. 1989. Triglycerides in embryogenic conifer calli: a comparison with zygotic embryos. Plant Cell Reports 8: 207–209.
4. Gupta, P. and J. A. Grob. (1995) Somatic Embryogenesis in Conifers. IN Somatic Embryogenesis of Woody Plants. Vol. I. S. M. Jain, P. K. Gupta, and R. J. Newton (Eds.) Kluwer Academic Publishers, Dordrecht, The Netherlands. pp. 81–98.
5. Heydecker, W. and Coolbear P. (1977) Seed treatment for improved performance-survey and attempt prognosis. Seed Science and Technology 5: 353–425.
6. Roberts, D. R., F. B. Webster, B. S. Flinn, W. R. Lazaroff & D. R. Cyr. 1993. Somatic embryogenesis of spruce IN: K. Redenbaugh (Ed.) Synseeds: Application of synthetic seeds to crop improvement. CRC Press, Boca Raton Fla. Pp. 427–452.
7. McDonald, M. B. 2000 Seed priming IN: Seed Technology and Its Biological Basis. M. Black & J. D. Bewley (Eds.) Sheffield Academic Press (in press).
8. Roberts. D. R. F. B. Webster, D. R. Cyr, T. K. Edmonds, S. M. A. Grimes & B. C. S. Sutton. (1995) In: J. Aitken-Christie, T. Kozai, and M. A. L. Smith (Eds.) Automation and Environmental Control in Plant tissue Culture Kluwer Academic Pub. Dordrecht, The Netherlands. pp. 245–256.
9. Sakamoto, Y., N. Onishi, and T. Hirosawa. (1995) Delivery Systems for Tissue Culture by Encapsulation. IN Automation and Environmental Control in Plant Tissue Culture. J. Aitken-Christie, T. Kozai, and M. L. A. Smith, Kluwer Academic Publishers, Dordrecht, The Netherlands. pp. 215–243.
10. Simon, E. W. (1984) Early events in germination. In Seed Physiology (D. R. Murray ed.) Academic Press. Toronto. pp. 77–115.

What we claim is:

1. A process of nutripriming gymnosperm somatic embryos prior to ex vitro sowing, comprising contacting imbibed, incompletely germinated gymnosperm somatic embryos with a liquid containing a dissolved nutrient, and maintaining said embryos in contact with said liquid in conditions and for a period of time that cause further imbibition of said liquid by said embryos and further germination.

2. The process of claim 1, wherein said nutrient is a carbohydrate.

3. The process of claim 1, wherein said nutrient is a sugar.

4. The process of claim 1, wherein said nutrient is sucrose.

5. The process of claim 4, wherein said sucrose is present in said liquid in an amount of 6% w/v or less.

6. A process of nutripriming gymnosperm somatic embryos prior to complete germination, comprising contacting imbibed, incompletely germinated gymnosperm somatic embryos with a liquid comprising a mixture of two or more dissolved nutrients, and maintaining said embryos in contact with said liquid in conditions and for a period of time that cause further imbibition of said liquid by said embryos and further germination.

7. The process of claim 6, wherein one of said nutrients is a sugar.

8. The process of claim 6 wherein one of said nutrients is sucrose.

9. The process of claim 8 wherein said sucrose is present in said liquid in an amount of 6% w/v or less.

10. The process of claim 6 wherein one of said nutrients is an amino acid.

11. The process of claim 6 wherein one of said nutrients is a nitrate ion.

12. The process of claim 6 wherein one of said nutrients is an ammonium ion.

13. The process of claim 6 wherein one of said nutrients is a phosphate ion.

14. The process of claim 6 wherein one of said nutrients is a potassium ion.

15. The process of claim 6 wherein one of said nutrients is a micronutrient.

16. The process of claim 6 wherein one of said nutrients is a vitamin.

17. The process of claim 6 wherein one of said nutrients is a plant growth regulator.

18. The process of claim 1, wherein said gymnosperm somatic embryo is from a tree species.

19. The process of claim 1, wherein said gymnosperm somatic embryo is a spruce embryo.

20. The process of claim 1, wherein said gymnosperm somatic embryo is an interior spruce embryo.

21. The process of claim 1, wherein said gymnosperm somatic embryo is a pine embryo.

22. The process of claim 1, wherein said gymnosperm somatic embryo is a loblolly pine embryo.

23. The process of claim 1 wherein said gymnosperm somatic embryo is a radiata pine embryo.

24. The process of claim 1 wherein said gymnosperm somatic embryo is a *Pinus patula* embryo.

25. The process of claim 6, wherein said gymnosperm somatic embryo is from a tree species.

26. The process of claim 6, wherein said gymnosperm somatic embryo is a spruce embryo.

27. The process of claim 6, wherein said gymnosperm somatic embryo is an interior spruce embryo.

28. The process of claim 6, wherein said gymnosperm somatic embryo is a pine embryo.

29. The process of claim 6, wherein said gymnosperm somatic embryo is a loblolly pine embryo.

30. The process of claim 6 wherein said gymnosperm somatic embryo is a radiata pine embryo.

31. The process of claim 6 wherein said gymnosperm somatic embryo is a *Pinus patula* embryo.

32. A method of producing seedlings or full-grown plants from gymnosperm somatic embryos, which comprises nutripriming gymnosperm somatic embryos by contacting imbibed, incompletely germinated gymnosperm somatic embryos with a liquid containing a dissolved nutrient, maintaining said embryos in contact with said liquid in conditions and for a period of time that cause further imbibition of said liquid by said embryos and further germination to form nutriprimed embryos, transferring said nutriprimed embryos ex vitro to a growth medium, further germinating the nutriprimed embryos in said growth medium to form germinants, and maintaining growing conditions to allow the germinants to grow into seedlings or full-grown plants.

33. The method of claim 32, wherein a nutrient is incorporated into said growth medium.

34. The method of claim 33, wherein the nutrient incorporated into the growth medium is the same as the nutrient used in the liquid.

35. The method of claim 32, wherein said further germinating of the nutriprimed embryos in said growth medium and said growing of said germinants are carried out in non-sterile conditions.

36. The method of claim 32, wherein the nutrient in the liquid is a carbohydrate.

37. The method of claim 32, wherein the nutrient in the liquid is a sugar.

38. The method of claim 32, wherein the nutrient in the liquid is sucrose.

39. The method of claim 38, wherein sucrose is present in said growth medium in an amount of 6% w/v or less.

40. The method of claim 32, wherein the gymnosperm somatic embryo is from a tree species.

41. The method of claim 32, wherein the gymnosperm somatic embryo is a spruce embryo.

42. The method of claim 32, wherein the gymnosperm somatic embryo is an interior spruce embryo.

43. The method of claim 32, wherein the gymnosperm somatic embryo is a pine embryo.

44. The method of claim 32, wherein the gymnosperm somatic embryo is loblolly pine embryo.

45. The method of claim 32, wherein the gymnosperm somatic embryo is a radiata pine embryo.

46. The method of claim 32, wherein the gymnosperm somatic embryo is a *Pinus patula* embryo.

47. A method of producing seedlings or full-grown plants from gymnosperm somatic embryos, which comprises nutripriming gymnosperm somatic embryos by contacting imbibed, incompletely germinated gymnosperm somatic embryos with a liquid containing a mixture of dissolved nutrients, maintaining said embryos in contact with said liquid in conditions and for a period of time that cause further imbibition of said liquid by said embryos and further germination to form nutriprimed embryos, transferring said nutriprimed embryos ex vitro to a growth medium, further germinating the nutriprimed embryos in a growth medium to form germinants, and maintaining growing conditions to allow the germinants to grow into seedlings or full-grown plants.

48. The method of claim 47, wherein a nutrient is incorporated into said growth medium.

49. The method of claim 48, wherein the nutrient incorporated into the growth medium is the same as the nutrient present in the liquid.

50. The method of claim 47, wherein said further germinating of the nutriprimed embryos in said growth medium and said growing of said germinants are carried out in non-sterile conditions.

51. The method of claim 47, wherein the nutrient incorporated into said growth medium is a carbohydrate.

52. The method of claim 47, wherein the nutrient incorporated into said growth medium is a sugar.

53. The method of claim 47, wherein the nutrient incorporated into said growth medium is sucrose.

54. The method of claim 53, wherein sucrose is present in said growth medium in an amount of 6% w/v or less.

55. The method of claim 47, wherein the gymnosperm somatic embryo is from a tree species.

56. The method of claim 47, wherein the gymnosperm somatic embryo is a spruce embryo.

57. The method of claim 47, wherein the gymnosperm somatic embryo is an interior spruce embryo.

58. The method of claim 47, wherein the gymnosperm somatic embryo is a pine embryo.

59. The method of claim 47, wherein the gymnosperm somatic embryo is loblolly pine embryo.

60. The method of claim 47, wherein the gymnosperm somatic embryo is a radiata pine embryo.

61. The method of claim 47, wherein the gymnosperm somatic embryo is a *Pinus patula* embryo.

62. A method of germinating mature gymnosperm somatic embryos, comprising priming imbibed, incompletely germinated gymnosperm embryos in the presence of a liquid containing a nutrient and maintaining said embryos in contact with said liquid in conditions and for a period of time that cause further imbibition of said liquid by said embryos and further germination.

63. The method of claim 62, wherein said nutrient is selected from the class comprising carbohydrates.

64. The method of claim 62, wherein said nutrient is selected from the class comprising sugars.

65. The method of claim 62, wherein said nutrient is sucrose.

66. The method of claim 65, wherein sucrose is present in said nutrient solution in a concentration of no greater than about 6% w/v.

67. The method of claim 62, wherein said nutrient is selected from the class comprising amino acids.

68. The method of claim 62, wherein at lest one additional nutrient is a nitrate ion.

69. The method of claim 62, wherein at least one additional nutrient is an ammonium ion.

70. The method of claim 62, wherein at least one additional nutrient is a phosphate ion.

71. The method of claim 62, wherein at least one additional nutrient is a potassium ion.

72. The method of claim 62, wherein at least one additional nutrient is selected from the class comprising micronutrients.

73. The method of claim 62, wherein at least one additional nutrient is selected from the class comprising vitamins.

74. The method of claim 62, wherein the nutrient medium further comprises a plant growth regulator.

75. The method of claim 62, wherein the gymnosperm somatic embryo is from a tree species.

76. The method of claim 62, wherein the gymnosperm somatic embryo is a spruce embryo.

77. The method of claim 62, wherein the gymnosperm somatic embryo is an interior spruce embryo.

78. The method of claim 62, wherein the gymnosperm somatic embryo is a pine embryo.

79. The method of claim 62, wherein the gymnosperm somatic embryo is loblolly pine embryo.

80. The method of claim 62, wherein the gymnosperm somatic embryo is a radiata pine embryo.

81. The method of claim 62, wherein the gymnosperm somatic embryo is a *Pinus patula* embryo.

82. A method of producing somatic gymnosperm seedlings, comprising (i) priming imbibed, incompletely germinated mature gymnosperm somatic embryos in a nutrient medium, maintaining said embryos in contact with said liquid in conditions and for a period of time that cause further imbibition of said liquid by said embryos and further germination, and (ii) sowing the embryos ex vitro in a sowing medium.

83. The method of claim 82, further comprising applying nutrients to the sown embryos.

84. The method of claim 83, wherein the means of applying nutrients to the sown embryos is selected from the group comprising spraying, misting, drenching, and irrigating.

85. The method of claim 82, wherein the plant somatic embryo is from a tree species.

86. The method of claim 82, wherein the plant somatic embryo is from a gymnosperm.

* * * * *